(12) United States Patent
Sweet et al.

(10) Patent No.: US 11,926,812 B2
(45) Date of Patent: Mar. 12, 2024

(54) PRESSURE-DRIVEN, ADJUSTABLE THROUGHPUT FLUIDICS FOR TISSUE AND CELL PERIFUSIONS

(71) Applicants: EnTox Sciences, Inc., Mercer Island, WA (US); University of Washington, Seattle, WA (US)

(72) Inventors: Ian Sweet, Mercer Island, WA (US); Gamal Khalil, Redmond, WA (US); Daniel Cook, Seattle, WA (US)

(73) Assignees: University of Washington, Seattle, WA (US); Entox Sciences, Inc., Mercer Island, WA (US)

( * ) Notice: Subject to any disclaimer, the term of this patent is extended or adjusted under 35 U.S.C. 154(b) by 180 days.

(21) Appl. No.: 16/769,569

(22) PCT Filed: Dec. 4, 2018

(86) PCT No.: PCT/US2018/063906
§ 371 (c)(1),
(2) Date: Jun. 3, 2020

(87) PCT Pub. No.: WO2019/113109
PCT Pub. Date: Jun. 13, 2019

(65) Prior Publication Data
US 2021/0163869 A1    Jun. 3, 2021

Related U.S. Application Data

(60) Provisional application No. 62/594,225, filed on Dec. 4, 2017.

(51) Int. Cl.
*C12M 1/00* (2006.01)
*C12M 1/34* (2006.01)
(Continued)

(52) U.S. Cl.
CPC ............ *C12M 29/10* (2013.01); *C12M 23/16* (2013.01); *C12M 23/42* (2013.01); *C12M 23/44* (2013.01); *C12M 29/14* (2013.01); *C12M 41/32* (2013.01)

(58) Field of Classification Search
CPC ...... C12M 29/10; C12M 23/16; C12M 23/42; C12M 23/44; C12M 29/14; C12M 41/32; G01N 33/5008
See application file for complete search history.

(56) References Cited

U.S. PATENT DOCUMENTS 4,918,019 A * 4/1990 Guinn .................... C12M 29/12
435/803
5,010,014 A * 4/1991 Gebhardt ............... C12M 41/22
435/297.2
(Continued)

OTHER PUBLICATIONS

"Perfusion Apparatus Model No. PER-05" Biorep Technologies, Inc., Miami, FL, p. 1-2, no date.
(Continued)

*Primary Examiner* — Liban M Hassan
(74) *Attorney, Agent, or Firm* — Seed IP Law Group LLP

(57) ABSTRACT

A microperifusion system includes at least one perifusate reservoir module having N receptacles and at least one port to communicate a pressurizing gas into or out from the respective perifusate reservoir module. A corresponding perifusion chamber module having M microperifusion channels is mechanically coupleable to at least one perifusate reservoir module to thereby form, when coupled, a sealed fluid communication between a selected first number of the N receptacles and a selected second number of the microperifusion channels. A control system module is coupleable to each perifusate reservoir and each perifusion chamber to control a flow of pressuring gas communicated into or out from the perifusate reservoir sense an effect of a microperi- (Continued)

fusion test operation occurring in each microperifusion channel.

4 Claims, 12 Drawing Sheets

(51) Int. Cl.
    *C12M 3/00*         (2006.01)
    *C12M 3/06*         (2006.01)

(56) References Cited

U.S. PATENT DOCUMENTS

| | | | | |
|---|---|---|---|---|
| 5,316,905 | A * | 5/1994 | Mori | C12M 29/26 435/297.1 |
| 6,197,575 | B1 * | 3/2001 | Griffith | G01N 33/5008 435/395 |
| 6,670,170 | B1 | 12/2003 | Gaffin et al. | |
| 8,263,389 | B2 | 9/2012 | Poo et al. | |
| 8,652,829 | B2 * | 2/2014 | Bellalou | G01N 35/0099 435/286.2 |
| 8,785,178 | B2 | 7/2014 | Poo et al. | |
| 8,865,427 | B2 | 10/2014 | Poo et al. | |
| 2005/0130297 | A1 * | 6/2005 | Sarem | C12M 23/12 435/297.1 |
| 2011/0007105 | A1 * | 1/2011 | Kuribayashi | B41J 2/17566 347/6 |
| 2013/0302894 | A1 * | 11/2013 | Bekele | B32B 27/08 428/483 |

OTHER PUBLICATIONS

"Perfusion Apparatus Model No. PER-53.2: User Manual," Biorep Technologies, Inc., Miami, FL, p. 1.21, no date.
"PIC32MZ Embedded Connectivity (EC) Family" Microchip Technology Inc., Chandler, AZ, p. 1-666, 2016.
Abu-Elheiga et al., "Continuous Fatty Acid Oxidation and Reduced Fat Storage in Mice Lacking Acetyl-CoA Carboxylase 2," *Science* 291:2613-2616, 2001.
Au et al., "3D-Printed Microfluidics," *Angewandte Chemie* 55:3862-3881, 2016.
Au et al., "Microvalves and Micropumps for BioMEMS," *Micromachines* 2(2):179-220, 2011.
Aziz et al., "Synthesis, single crystal analysis, biological and docking evaluation of tetrazole derivatives," *Heliyon* 4:e00792, 2018.
Bavli et al., "Real-time monitoring of metabolic function in liver-on-chip microdevices tracks the dynamics of mitochondrial dysfunction," *Proc. Natl. Acad. Sci.* 113:E2231-2240, 2016.
Bennett et al., "Chapter 7. Concepts of Fluid Behavior (I)," in *Momentum, Heat, and Mass Transfer*, McGraw-Hill, New York, New York, USA, 1962. (pp. 61-63 only).
Bhattacharjee et al., "The upcoming 3D-printing revolution in microfluidics," *Lab Chip.* 16(10):1720-1742, 2016.
Biorep Diabetes, "All Products," URL = http://www.biorepdiabetes.com/shop/, version accessed Aug. 4, 1 page, 2020.
Brennan et al., "A 3D-Printed Oxygen Control Insert for a 24-Well Plate," *PLoS One* 10:e0137631, 2015.
Brennan et al., "Oxygen control with microfluidics," *Lab Chip* 14:4305-4318, 2014.
Cerroni et al., "In vivo biological fate of poly(vinylalcohol) microbubbles in mice," *Heliyon* 4:e00770, 2018.
Chang et al., "Parallel Microfluidic Chemosensitivity Testing on individual Slice Cultures," *Lab Chip* 14(23):4540-4551, 2014.
Cooksey et al., "A multi-purpose microfluidic perfusion system with combinatorial choice of inputs, mixtures, gradient patterns, and flow rates," *Lab Chip* 9(3):417-426, 2009.
Coyac et al., "Periodontal reconstruction by heparin sulfate mimetic-based matrix therapy in *Porphyromonas gingivalis*-infected mice," *Heliyon* 4:e00719, 2018.

Davis et al., "Pyruvate Carboxylase and Propionyl-CoA Carboxylase as Anaplerotic Enzymes in Skeletal Muscle Mitochondria," *Eur. J. Biochem.* 110: 255-262, 1980.
Doliba et al., "Cholinergic regulation of fuel-induced hormone secretion and respiration of SUR1$^{-/-}$ mouse islets," *Am. J. Physiol. Endocrinol. Metab.* 291:E525-535, 2006.
Ehmann et al., "CO2/bicarbonate stimulates growth independently of PH in mouse mammary epithelial cells," *In Vitro* 19:767-774, 1983.
Farjadian et al., "A novel approach to the application of hexagonal mesoporous silica in solid-phase extraction of drugs," *Heliyon* 4:e00930, 2018.
Gerencser et al., "Quantitative Microplate-Based Respirometry with Correction for Oxygen Diffusion," *Anal. Chem.* 81:6868-6878, 2009.
Henquin et al., "Bicarbonate modulation of glucose-induced biphasic insulin release by rat islets," *Am. J. Physiol.* 231:713-721, 1976.
Henquin et al., "Extracellular bicarbonate ions and insulin secretion," *Biochim. Biophys. Acta.* 381:437-442, 1975.
Hoshi et al., "Production of hollow-type spherical bacterial cellulose as a controlled release device by newly designed floating cultivation," *Heliyon* 4:e00873, 2018.
International Preliminary Report on Patentability, dated Jun. 9, 2020, for International Application No. PCT/US2018/063906, 5 pages.
Jean et al., "Design, synthesis and evaluation of novel 2,2-dimethyl-2,3,-dihydroquinolin-4(1H)-one based chalcones as cytotoxic agents," *Heliyon* 4:e00767, 2018.
Khuc et al., "Using β-lactamase and NanoLuc Luciferase Reporter Gene Assays to Identify Inhibitors of the HIF-1 Signaling Pathway," *Methods Mol. Biol.* 1473:23-31, 2016.
Kumar et al., "Antitumour, acute toxicity and molecular modeling studies of 4-(pyridin-4-yl)-6-(thiophen-2-yl) pyrimidin-2(1H)-one against Ehrlich ascites carcinoma and sarcoma-180," *Heliyon* 4:e0061, 2018.
Kumar et al., "Design, synthesis, biological evaluation, and molecular docking studies of novel 3-substituted-5-[(indol-3-yl)methylene]-thiazolidine-2,4-dione derivatives," *Heliyon* 4:e00807, 2018.
Leclerc et al., "Microfluidic PDMS (polydimethylsiloxane) bioreactor for large-scale culture of hepatocytes," *Biotechnol. Prog.* 20:750-755, 2004.
Matsumoto et al., "Immediate reversal of diabetes in primates following intraportal transplantation of porcine islets purified on a new histidine-lactobioniate-iodixanol gradient," *Transplantation* 67(7):S220, 1999.
Mestres et al., "The Bionas technology for anticancer drug screening," *Expert Opin. Drug Discov.* 4:785-797, 2009.
Mitaka et al., "The bicarbonate ion is essential for efficient DNA synthesis by primary cultured rat hepatocytes," *In Vitro Cell. Dev. Bio.—Animal* 27:549-556, 1991.
Neal et al., "Quantification of Low-Level Drug Effects Using Real-Time, in vitro Measurement of Oxygen Consumption Rate," *Toxicol. Sci.* 148(2):594-602, 2015.
Pfitzner, "Poiseuille and his law," *Anaesthesia* 31:273-275, 1976.
Rountree et al., "BaroFuse, a novel pressure-driven, adjustable-throughput perfusion system for tissue maintenance and assessment," *Heliyon* 2:e00210, 2016.
Sala-Vila et al., "Interplay between hepatic mitochondria-associated membranes, lipid metabolism and caveolin-1 in mice," *Sci. Rep.* 6(27351):1-10, 2016.
Schmidt et al., "In vitro acute and developmental neurotoxicity screening: an overview of cellular platforms and high-throughput technical possibilities," *Arch. Toxicol.* 91(1):1-33, 2016.
Singh et al., "Xanthine scaffold: scope and potential in drug development," *Heliyon* 4:e00829, 2018.
Sutera et al., "The History of Poiseuille's Law," *Annu. Rev. Fluid Mech.* 25:1-20, 1993.
Sweet et al., "Continuous measurement of oxygen consumption by pancreatic islets," *Diabetes Technol. Ther.* 4:661-672, 2002.
Sweet et al., "Contribution of Calcium Influx in Mediating Glucose-Stimulated Oxygen Consumption in Pancreatic Islets," *Diabetes* 55:3509-3519, 2006.

(56) References Cited

OTHER PUBLICATIONS

Sweet et al., "Dynamic perifusion to maintain and assess isolated pancreatic islets," *Diabetes Technol. Ther.* 4:67-76, 2002.
Sweet et al., "Glucose Stimulation of Cytochrome C Reduction and Oxygen Consumption as Assessment of Human Islet Quality," *Transplantation* 80:1003-1011, 2005.
Sweet et al., "Regulation of ATP/ADP in Pancreatic Islets," *Diabetes* 53:401-409, 2004.
Tolosa et al., "High-content screening technology for studying drug-induced hepatotoxicity in cell models," *Archives of Toxicology* 89:1007-1022, 2015.
Utter et al., "Formation of Oxaloacetate from Pyruvate and $CO_2$," *J. Biol. Chem.* 235(5):PC17-PC18, 1960.
Van Midwoud et al., "A microfluidic approach for in vitro assessment of interorgan interactions in drug metabolism using intestinal and liver slices," *Lab Chip* 10:2778-2786, 2010.
Wikipedia, "Hagen-Poiseuille equation," URL = https://en.wikipedia.org/wiki/Hagen%E2%80%93Poiseuille_equation, version accessed Aug. 4, 8 pages, 2020.
Wikstrom et al., "A novel high-throughput assay for islet respiration reveals uncoupling of rodent and human islets," *PLoS One* 7(5):e33023, 2012.
Zhang et al., "Water absorption by decellularized dermis," *Heliyon* 4:e00600, 2018.
Zhao et al., "Cell-based assay for identifying the modulators of antioxidant response element signaling pathway," *Methods Mol. Biol.*: High Throughout Screen Assays in Toxicology 1473:55-62, 2016.

\* cited by examiner

PRESSURE-DRIVEN, ADJUSTABLE THROUGHPUT FLUIDICS FOR TISSUE AND CELL PERIFUSIONS

STATEMENT OF GOVERNMENT INTEREST

This invention was made with government support under Grant Nos. P30 DK017047 and R41 TR001196, awarded by the National Institutes of Health. The government has certain rights in the invention.

BACKGROUND

Technical Field

The present disclosure generally relates to microfluidic perifusion systems. More particularly, but not exclusively, the present disclosure relates to microfluidic perifusion systems that assess cell and tissue function while sustaining cellular viability.

Description of the Related Art

Studying the cellular response to controlled stimulus can yield important information about the cells and the effect of the stimulus on the cells. This information can be used in research for the development and validation of new pharmaceuticals, fertilizers, industrial compounds, and the like. This information can also be used to learn about and better understand the response, reaction, adaptation, health, and even the viability of the cells when exposed to any number of elements, compounds, and environmental conditions.

One method to study the response of cells to various stimuli is perifusion. Perifusion may be described as a process by which a fluid is passed by cells or tissue immersed in the fluid. In some known perifusion devices, a column has input and output tubing. The cells or tissue of interest are placed into the column, and a solution having the element or compound "stimulus" is permitted to flow. Periodic samples are drawn from the column via the outlet tube and tested. The process using such a device takes significant time and special preparations that are often manually performed. Nevertheless, the resultant data is valuable and reproducible, so these procedures persist in both commercial and academic environments.

At least one known perifusion device has a chamber, an inlet to the chamber to receive liquid, and an outlet from the chamber to discharge material for testing. A fraction collector is connected to the chamber or to a plurality of receptacles for collecting the discharged material. The perifusion device also has a plurality of sample containers positioned to provide samples to the plurality of receptacles that collect the discharged material. The sample containers are arranged as columns packed with a substrate of any suitable form, such as beads or gel. A peristaltic pump is used to force a controlled volume and rate of test liquid to flow through chamber and thus the columns. After passing the test liquid through the device, a sensor measures a characteristic of the resultant fluid.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

BRIEF SUMMARY

The inventors of the present application have recognized that conventional perifusion systems are expensive and time consuming to operate for the production of academically and commercially valuable information. The conventional systems are not easily scalable into larger systems, and the conventional systems are limited in the type of testing that can be performed. Often, tissue or cell structures placed in the conventional systems have a short, un-sustained life cycle, which limits many types of tests that are desirably conducted over hours or days.

The inventors recognized problems with conventional systems and set forth to create scalable microfluidic perifusion systems, devices, and methods for assessing cell and tissue function with assurance that cellular viability is sustained. The embodiments described in the present disclosure permit low perifusate flow rates that enable economy and extended-duration experiments. Additionally, the embodiments remove the need for the peristaltic pumps that are used in conventional systems. Accordingly, the embodiments of the present disclosure are suitable for both single channel testing and high-throughput applications that implement 16, 96, or even more channels. And these embodiments describe scalable, multi-channel microfluidics systems, devices, and methods capable of maintaining and assessing kinetic responses of small amounts of tissue to drugs or changes in test conditions.

In some embodiments, a multi-channel microfluidics device is fabricated using three-dimensional (3D) printing technology arranged, via gas pressure, to drive any suitable numbers of parallel perifusion experiments. These devices are versatile with respect to endpoints due to a translucence of the walls of the perifusion chambers, which enable the application of optical structures and methods to interrogate the tissue status. In at least some embodiments, an oxygen detection system is incorporated to enable continuous measurement of an oxygen consumption rate (OCR).

In some embodiments, stable and low flow rates (e.g., less than 0.1 µL/min/channel to 200 µL/min/channel) are finely controlled by a single pressure regulator (e.g., ≈0.5 psi to ≈2.5 psi). Control of flow in 0.2 µL/min increments is achieved in some embodiments. In some embodiments, the enabled low flow rates permit OCR changes, in response to glucose for example, to be well resolved with very small numbers of islets (e.g., 1-10 islets/channel). In some embodiments, the low flow rates and structural arrangement of the systems and devices allow for the efficient generation of a large number (e.g., tens, hundreds, thousands) of kinetic profiles in OCR and other endpoints that last minutes, hours, or days. In some embodiments, elements of the native three-dimensional structure of the tissue under test are preserved.

Contrary to conventional perifusion systems, embodiments described in the present disclosure are powerful tools useful for physiological studies, pharmacological studies, pharmaceutical assessment of drug effects, personalized medicine, and other reasons that will be made clear to ones of ordinary skill in the art. Embodiments are arranged, for example, as one or more scalable-throughput fluidics systems that can be operated to maintain and assess primary tissue. The embodiments can be operated at low flow rates to conserve tissue, media and test compounds. At least one embodiment is arranged to resolve glucose responses in oxygen consumption rate (OCR) by one (1) islet/channel. At least one embodiment is arranged to generate dose-dependent responses of acetaminophen on OCR by liver tissue.

A microperifusion method may be summarized as including: providing a perifusate reservoir module, the perifusate reservoir module having N receptacles, and the perifusate reservoir module having at least one port arranged to communicate a pressurizing gas into or out from the perifusate reservoir module; providing a perifusion chamber module, the perifusion chamber module having M microperifusion channels; providing a control system module, the control system module having at least M sensor systems and at least one valve control mechanism, the at least one valve control mechanism arranged to control communication of the pressurizing gas; adding a liquid perifusate material to each of the N receptacles; mechanically coupling the perifusate reservoir module to the perifusion chamber module, the mechanical coupling forming a gasketed seal between selected ones of the N receptacles and corresponding ones of the M microperifusion channels; and electromechanically coupling the control system module to the perifusion chamber module, said electromechanical coupling causing each of the M sensor systems to be located in proximity to a respective one of the M microperifusion channels, said electromechanical coupling providing an electronic signal path to carry control signals to at least one valve.

The microperifusion method may further include: adding at least one sample of biological material to each of the M microperifusion channels; adding at least one dye to each of the M microperifusion channels; and executing at least one microperifusion test cycle, the at least one microperifusion test cycle spanning a selected time duration. The microperifusion method may further include: directing a first valve to increase pressure in the perifusate reservoir module, the increased pressure causing at least some of the liquid perifusate material to flow in at least one of the M microperifusion channels; directing a first sequence of source signals to be emitted from at least one source sensor of the at least M sensor systems, the first sequence of source signals passing into the liquid perifusate material flowing in the at least one of the M microperifusion channels; directing a first response sensor that is paired with a corresponding source sensor of the at least M sensor systems to measure a first sequence of response signals, each one of the first sequence of response signals responsive to at least one of the first sequence of source signals; and generating at least one value based on an accumulation of the measured response signals, the at least one value representative of a determined property of the liquid perifusate material flowing in the at least one of the M microperifusion channels. The at least one value may indicate an oxygen consumption rate of the at least one sample of biological material. A flow rate of the liquid perifusate material flowing in the at least one of the M microperifusion channels may be between about one-tenth microliter per minute and about 200 microliters per minute.

A microperifusion system may be summarized as including: at least one perifusate reservoir module, each of the at least one perifusate reservoir modules having N receptacles, and each of the at least one perifusate reservoir modules having at least one port arranged to communicate a pressurizing gas into or out from the respective perifusate reservoir module; for each of the at least one perifusate reservoir modules, a corresponding perifusion chamber module, each corresponding perifusion chamber module having M microperifusion channels, and each corresponding perifusion chamber module mechanically coupleable to one of the at least one perifusate reservoir modules to thereby form, when coupled, a sealed fluid communication between a selected first number of the N receptacles and a selected second number of the M microperifusion channels; and a control system module coupleable to each of the at least one perifusate reservoir modules and coupleable to each of the corresponding perifusion chamber modules, said control system module, when in operation, arranged to: control a flow of pressuring gas communicated into or out from the perifusate reservoir module; and sense an effect of a microperifusion test operation occurring in each of the M microperifusion channels.

The sensed effect may be an oxygen consumption rate of at least one sample of biological material in at least one of the M microperifusion channels. The control system module may further include: pressure control logic to cause a perifusate material flowing in at least one of the M microperifusion channels to flow a selected rate of between about one-tenth microliter per minute and about 200 microliters per minute. N may be at least two times larger than M. The control system module may further include: a system of source sensors and response sensors, each response sensor pairable with a corresponding source sensor, and each response sensor arranged to capture light signal measurements responsive to light emitted by its corresponding source sensor; control logic arranged to direct each source sensor to emit light at a first selected time, the control logic further arranged to direct each response sensor to capture light signal measurements based on a second selected time; and math logic arranged to determine a rate of decay from the captured light signal measurements, the rate of decay indicative of the sensed effect.

A control system for a microperifusion system may be summarized as including: a sensor system, the sensor system including a plurality of source sensors and a plurality of response sensors, each source sensor pairable with a corresponding response sensor, each source sensor/response sensor pair arranged to communicate through a microperifusion channel; and at least one processor communicatively coupled to each source sensor/response sensor pair, the at least one processor arranged to execute a test cycle having a determined duration, wherein during the test cycle, the at least one processor is arranged to: direct a valve system to pressurize at least one receptacle of a perifusate reservoir, the perifusate reservoir having a plurality of N receptacles, the perifusate reservoir coupled to a microperifusion chamber in sealed fluid communication, the microperifusion chamber having a plurality of M microperifusion channels, said pressurized receptacle arranged to deliver a perifusate material to a respective one of the M microperifusion channels at a selected flow rate of less than about one-tenth microliter per minute to about 200 microliters per minute ($<\approx 0.1$ μL/min to $\approx 200$ μL/min); direct a first sequence of source signals to be emitted from a first source sensor located in proximity to the respective one of the M microperifusion channels, the first sequence of source signals passing into a first perifusate material flowing at the selected flow rate in the respective one of the M microperifusion channels; direct a first response sensor that is paired with the first source sensor to measure a first sequence of response signals, each one of the first sequence of response signals responsive to at least one of the first sequence of source signals; and generate at least one value based on an accumulation of the measured response signals, the at least one value representative of a determined property of the first perifusate material flowing at the selected flow rate in the respective one of the M microperifusion channels.

The test cycle may be arranged for a continuous assessment of living biological material over a selected duration. This selected duration can be any value within the range of several hours to several weeks, with a duration of 4 weeks being useful in some embodiments. In some instances the selected duration may be several months. One acceptable duration falls within range of 25 to 35 days, with 28 days being selected for the duration in some embodiments. The determined property may be an oxygen consumption rate of at least one sample of biological material in at least one of the M microperifusion channels. N may be at least two times larger than M. M may be at least 96. The N receptacles may be disposable receptacles. The perifusate reservoir may be disposable. The at least one processor may be further arranged to: direct the valve system to pressurize the perifusate reservoir to cause a first receptacle of the plurality of N receptacles, to deliver a test perifusate material into the at least one receptacle, wherein the at least one receptacle has a control perifusate material stored therein. A first conduit between the first receptacle and the at least one receptacle may have a first inside diameter, a second conduit between the at least one receptacle and an associated microperifusion channel has a second diameter, and the first diameter is larger than the second diameter. The microperifusion chamber may be formed, at least in part, from a three-dimensional solid stereolithography process.

These features with other objects and advantages, which will become subsequently apparent, reside in the details of construction and operation as more fully described hereafter and claimed, reference being had to the accompanying drawings forming a part hereof.

This Brief Summary has been provided to introduce certain concepts in a simplified form that are further described in detail below in the Detailed Description. Except where otherwise expressly stated, the Brief Summary does not identify key or essential features of the claimed subject matter, nor is it intended to limit the scope of the claimed subject matter.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

Figure 1:
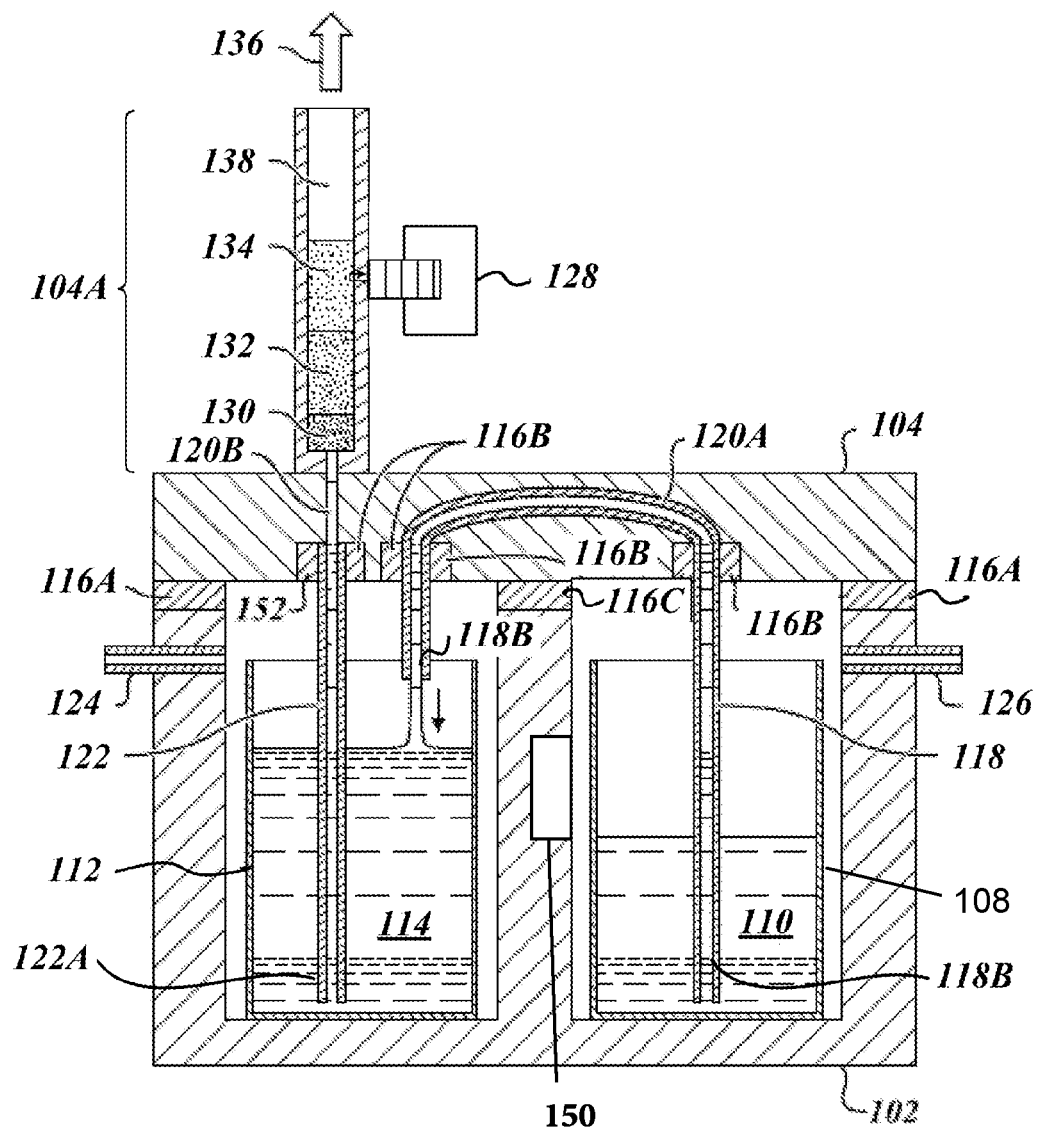
FIG. 1 is a detailed embodiment illustrating the operation of a perifusate reservoir module coupled to a single channel of a microperifusion chamber module.

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computing systems including client and server computing systems, as well as networks have not been shown or described in detail to avoid unnecessarily obscuring descriptions of the embodiments.

Prior to setting forth the embodiments however, it may be helpful to an understanding thereof to first set forth descriptions of certain terms that are used hereinafter.

The term "perfusion" generally relates to pumping or otherwise advancing a liquid (i.e., a perfusate) into an organ or tissue, especially by way of blood vessels. Perfusion may, for example, be used to introduce a drug, nutrient, or other substance into the bloodstream in order to reach an internal organ or tissue. Along these lines, perfusion may be understood as the passage of fluid through the circulatory or lymphatic system to an organ or a tissue, such as via the delivery of blood to a capillary bed in tissue.

The term "perifusion" generally relates to fluid flow (i.e., a perifusate); especially that of a solution of drugs, or a suspension of cells in a biological in vivo or in vitro system.

The two terms, perfusion and perifusion, are similar and for the sake of the present disclosure, may be better understood by their respective prefix in addition, or in the alternative, by their use in context. "Per," for example, may be understood to mean "through," as in the exemplary word, "permeable." "Peri," for example, may be understood to me "about," "around," "enclosing," "surrounding," "near," or another like term. Exemplary words may include, "perimeter," "periscope," pericardium," "perigee," and "perihelion,"

In both cases, perfusion and perifusion may be measured as the rate at which blood or another liquid (i.e., a perfusate or perifusate, as the case may be) is delivered to tissue, or volume of blood or another liquid per unit time per unit tissue mass. The International System of Units (SI) unit for perfusion and perifusion may be cubic meters per second ($m^3/s$). Units in the present disclosure may be reported as milliliters per minute per gram (ml/min/g) of perfusate or perifusate flow.

Scientific practitioners (i.e., scientists, technicians, operators, researchers, or the like) of many disciplines, which include but are not limited to, physiologists, pharmacologists, biologists, pathologists, chemists, and many others, have a desire to assess cell and tissue function. Many approaches to the study of cell and tissue function are being taken including any number and combination of cell-based assays of cell viability (e.g., apoptosis and necrosis), morphology and function, and the like. Many static incubation methods are well suited to high throughput application, but these static incubation methods are not capable of high-throughput kinetic measurements that operate over minutes, hours and days while maintaining the three-dimensional (3D) architecture of the tissue with sufficient integrity. Even though some conventional dynamic flow-through methods offer a combination of "optimal" tissue maintenance with assay endpoints, these methods typically depend on peristaltic pumps and complex "plumbing" schemes that are not practically scalable for high-throughput applications. Rather, for high-throughput applications such as pharmaceutical drug screening, toxicity testing, and others, the present inventors have developed and validated a simplified and scalable perifusion solution.

Early in the development process, the present inventors recognized several problems that prevented lab-based conventional single channel, flow-through cell/tissue perifusion systems from scaling up into commercially viable, multi-channel perifusion systems. A first problem is that the peristaltic pumps and complex tubing arrangements of conventional systems do not provide sufficiently consistent pressure and flow rates of liquid medium when scaled. All known attempts to scale the conventional technologies over many channels resulted in systems having many added peristaltic pumps, additional complex tubing, or both. Hence, these early attempts to scale the conventional technology resulted in overly complex, large, unreliable, duplicative, and expensive systems. A second problem is that the performance of conventional systems drops at lower flow rates. The inventors' desire was to create a new perifusion system with lower flow rates in order to reduce the consumption, per unit time, of media, test compounds, and tissue. Embodiments of the systems described in the present disclosure provide stable and low perifusate flows of about one-tenth to two hundred microliters per minute (0.1-200 µL/min) driven by gauge pressures between zero and about 2.5 pounds per square inch (0 and $\approx$2.5 psi) of a pH-buffered physiological gas such as a mixture of about five percent carbon dioxide and ambient air ($\approx$5% $CO_2$, balance air) that overlies separate perifusate reservoirs. Lower and higher flow rates, higher gauge pressures, and different physiological gas and gas mixtures are separately and combinatorily contemplated. While affording acceptably rapid changes of perifusate composition (e.g., on the order of minutes), perifusion cycles of nearly any type can be extended to many hours and even many days while sustaining the cellular and/or tissue integrity of the sample under test, and further while continuously recording a variety of biochemical and biophysical responses.

To address the shortcomings of the conventional technology, and to overcome the problems encountered when trying to scale the conventional technology, the inventors first created a new system having a microperifusion module and a perifusate reservoir module.

FIG. 1 is a detailed embodiment illustrating the operation of a perifusate reservoir 102 module coupled to a single channel 104A of a microperifusion chamber module 104.

Figure 2:
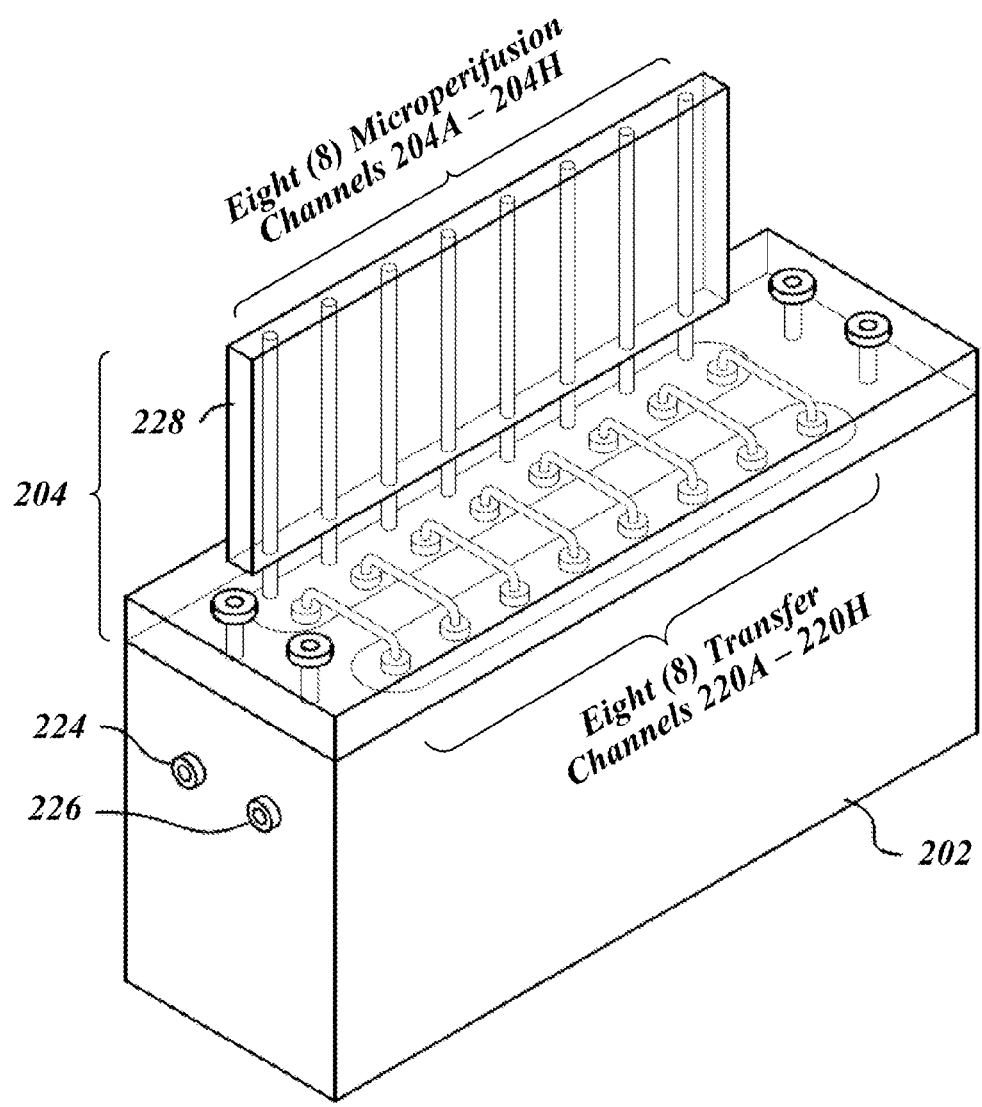
FIG. 2 is a microperifusion chamber embodiment having eight microperifusion channels coupled to a multi-channel, multi-perifusate receptacle reservoir.

FIG. 2 is a microperifusion chamber 204 embodiment having eight microperifusion channels 204A-204H coupled to a multi-channel, multi-perifusate receptacle reservoir 202, and an opto-electronics module 228 is coupled to the microperifusion chamber 204. The microperifusion chamber 204 of FIG. 2 is representative of an actual prototype constructed and tested by the inventors. In the prototype, and in other embodiments of modular microperifusion chambers described herein, each microperifusion channel may be arranged at a suitable distance from one or more adjacent microperifusion chambers. The distance between adjacent microperifusion channels may be based on light passed into, from, or into and from the microperifusion channel during analysis of material in the respective channel.

In at least some embodiments, each microperifusion channel is about one half inch ($\approx$0.5 in.) from adjacent microperifusion channels. In other embodiments, each microperifusion channel is less than one half inch (<0.5 in.) from other microperifusion channels. The "walls" of the microperifusion channels in some cases are about three millimeter ($\approx$3 mm) thick, though walls of other thicknesses are contemplated. The microperifusion chamber in embodiments described in the present disclosure is constructed from a plastic material, an acrylic material, a composite material, a glass, or some other material. The microperifusion chamber 204 of the specific prototype embodiment of FIG. 2 is a proprietary material (e.g., WATERSHED XC 11122, for example, used in a stereolithography (3D printing) process by PROTO LABS, INC.).

The opto-electronics module 228 is arranged in the embodiment of FIG. 2 to include a light-emitting diode (LED)/photoelectric diode (PED) pair structurally located about each of the eight microperifusion channels. At selected times, an LED will emit light into its respective channel, and the corresponding PED will measure received light. Some of the LED-emitted light may strike the PED, some reflected light may strike the PED, some ambient light may strike the PED, and some light generated by a photo-sensitive dye arranged in the channel will strike the PED. The light generated by the photo-sensitive dye is responsive to a reaction (e.g., chemical, biological, physiological, or the like) caused by the perifusate material in the chamber flowing about the tissue or cell sample in the chamber. By capturing, with the PED, a plurality of light sample measurements, certain conclusions about the interaction between the perifusate material and the tissue or cell sample material may be concluded, inferred, or otherwise determined.

The eight-channel prototype of FIG. 2 was used to validate the scalability of a modularized microperifusion system as illustrated and described in the present disclosure.

In at least one embodiment, such as in the prototype embodiment of FIG. 2, a pressure-driven, adjustable throughput fluidics (pressure-driven, adjustable throughput fluidics) system is arranged with a first plurality of modules; each of the plurality of modules having a second plurality of channels. Such a pressure-driven, adjustable throughput fluidics system may have, for example, twelve (12) modules, each module having eight (8) channels, for a total of 96 separate and distinct channels. The first plurality of modules can be arranged as rows, columns, arrays, or in any other suitable manner. The second plurality of channels can be arranged as rows, columns, arrays, or in any other suitable manner.

In some cases, the pressure-driven, adjustable throughput fluidics system is arranged to study cultured tissues such as liver slices, pancreatic islets, and the like. In some cases, the pressure-driven, adjustable throughput fluidics system is arranged to study cultured cells immobilized on, or distributed within, a slurry of culture beads. The cultured tissues, cells, or other samples under test may be initially provided in a microgram quantity (e.g., 1 µg, 10 µg, 50 µg or some other quantity).

In at least one case, a pressure-driven, adjustable throughput fluidics system prototype developed by the present inventors has been fabricated using 3D solid stereolithography. This prototype has also been validated against known results of physiological and drug testing. The pressure-driven, adjustable throughput fluidics prototype system is modular and extensible and includes an 8-channel module as a basic building block. Any number of 8-channel modules can be readily multiplexed to form systems having many separate and distinct channels (e.g., 32, 96, 256, and more). Within the pressure-driven, adjustable throughput fluidics prototype system, perifusate flow is pulse-free, substantially invariant from channel-to-channel, and acceptably stable (e.g., less than 2% drift) for any determined number of minutes, hours, and days. Flow rate is controlled in the range from less than about 0.1-200 µL/min per channel, which reduces the consumption of tissue, perifusate, and test compounds. Other flow rates are contemplated. In the pressure-driven, adjustable throughput fluidics prototype system, the perifusate is medically sterile and maintained at about 37 degrees Celsius ($\approx 37°$ C.) or less while physiologically gassed (e.g., with 5% $CO_2$ balance air or another gas) to sustain cellular bicarbonate ($H_2CO_3$). It has been recognized that certain cell physiological functions are lost when buffers void of $CO_2$ are used. Operational complexity and speed of use of the pressure-driven, adjustable throughput fluidics prototype system has been determined by the inventors to be on par with other known cell and tissue testing methods.

Considering the one pressure-driven, adjustable throughput fluidics system prototype case introduced herein and illustrated in FIG. 2, the present inventors have determined that high-throughput tissue testing can be performed with a reduced requirement and expense of isolating large amounts of tissue and of preparing large amounts of drug-containing perifusates. For example, a typical study of oxygen consumption rate (OCR) by perifused islets required 500-750 islets per channel with perifusate flows of 50-100 µL/min. Conversely, static incubation systems produced by SEAHORSE BIOSCIENCE, for example, may require 50-80 islets per well. In the pressure-driven, adjustable throughput fluidics system prototype, however, acceptably robust and reproducible OCR measurements can be made using only 1-10 islets per channel. Such economy is practical for high-throughput studies given the islet counts in a mouse (n$\approx$250) or rat (n$\approx$750). Accordingly, a 96-channel experiment may be carried out with a few hundred islets, obtainable with a single mouse or rat. The present inventors have tested stable flow rates of three microliters per minute (3 µL/min), which have been executed for 48 hours from a nine milliliter (9 mL) perifusate reservoir. Along these lines, the present inventors have determined that tests could be run for much longer than 48 hours by increasing the volumetric capacity of the perifusate reservoir module.

pressure-driven, adjustable throughput fluidics system embodiments, which provide dynamically flowing liquid about a biological sample under study, offer distinct advantages over non-flowing systems. One such advantage is that pressure-driven, adjustable throughput fluidics systems can maintain and assess cell function over a test cycle that spans any desirable number of minutes, hours, or days. Oxygen delivery is better, especially for tissue and multi-cellular structures in the pressure-driven, adjustable throughput fluidics system embodiments of the present disclosure, and flow of the liquid medium allows for an acceptably precise determination of consumption or production of chemical entities, wherein such determination may be determined, for example, based on the conservation of mass as the difference between the contents of the outflow minus the inflow. Accordingly, in at least some embodiments, an oxygen consumption rate may be determined (e.g., measured, calculated, predicted, or otherwise determined) with an acceptably high sensitivity and reproducibility over many tests runs. Hence, the pressure-driven, adjustable throughput fluidics system embodiments described herein are arranged to record the dynamic responses of a biological sample under study to test compounds in ways that are not available with static incubation systems.

In at least some pressure-driven, adjustable throughput fluidics system embodiments, the pressurized gas that drives perifusate flow containing 5% $CO_2$ is pH-buffered physiologically. This is useful because bicarbonate/$CO_2$ buffering is essential for a variety of biochemical functions such as gluconeogenesis, fatty acid synthesis, insulin secretion, and the citric acid cycle, among others. This gas is also useful to sustain cell growth and replication. By providing near physiological, flow-through conditions in the perifusion chambers described in the present disclosure, experiments of a long duration (e.g., many minutes, hours, or days) can be performed, which is useful for studying both acute and slow test substance (e.g., drug) effects.

In FIG. 1, a perifusate reservoir 102 includes a plurality of perifusate receptacles (i.e., a first receptacle, a second receptacle, and so on). In other embodiments, a perifusate reservoir 102 will include one perifusate receptacle, three perifusate receptacles, or some other number of perifusate receptacles. In FIG. 1, the first perifusate receptacle 108 of perifusate reservoir 102 is arranged to store a test perifusate material 110; the second perifusate receptacle 112 is arranged to store a control perifusate material 114.

In at least some embodiments, each perifusate receptacle is a test tube, a flask, or another receptacle having a standard or proprietary size and shape. Prior to beginning a test cycle, the perifusate receptacles of interest can be placed into respective compartments in the perifusate reservoir 104. In this way, any number of desired receptacles can be totally or partially filled (e.g., poured, dripped, placed, or the like) with a perifusate of interest in advance of beginning a test cycle. The receptacles may be disposable. Alternatively, the receptacles may be reusable. In at least one embodiment, the receptacles are test tubes nominally measuring 13 millimeters (mm) wide and 100 mm long (13×100 mm) and having a volume of nine milliliters (9 mL).

In other embodiments, each perifusate receptacle (e.g., first and second perifusate receptacles 108, 112) is integrated into the perifusate reservoir 102. In these embodiments, the entire perifusate reservoir 102 may be disposable or reusable.

As illustrated in FIG. 1, the perifusate reservoir 102 is removably or fixedly coupled to the microperifusion chamber 104. One or more gaskets 116A-116C are arranged at the interface between the perifusate reservoir 102 and the microperifusion chamber 104. Gaskets 116A-116C may be arranged as a single gasket or a plurality of gaskets. Gaskets 116A-116C may be a gasket material (e.g., a rubber-based material, a silicone-based material, or the like) painted or otherwise spread at the interface. The gasket material seals internal structures of the perifusate reservoir 102 module and the microperifusion chamber module 104 from the outside atmosphere, thereby creating a system that permits pressure to finely control the flow of perifusate material.

At least some of the gaskets 116A-116C represented in FIG. 1 may be optional in various embodiments. In particular, gaskets 116A that border the outside perimeter of the interface between perifusate reservoir 102 and microperifusion chamber 104 are always present to seal the internal structures of the modules from the outside atmosphere. These necessary outside perimeter gaskets 116A permit the internal structures of the system to become pressurized. In addition, or in the alternative, at least some of the internal gaskets 116B, 116C are optional. When the appropriate gaskets 116A-116C are present, each separate and distinct receptacle (e.g., the first and second perifusate receptacles 108, 112 of FIG. 1) may be individually pressurized. On the other hand, if appropriate optional gaskets 116B, 116C are omitted, two or more of the perifusate receptacles may be pressurized in common via a single pressurized port.

In cases where various receptacles of the perifusate reservoir 102 are separately pressurized, once the perifusate reservoir 102 is sealed, a first perifusate receptacle 108 for example may be pressurized to a first pressure, and a second perifusate receptacle 112 may be pressurized to a second pressure, wherein the first pressure is different from the second pressure. This differential pressure may cause perifusate material to flow from one receptacle to another receptacle.

In cases where at least some gaskets 116B, 116C are omitted, a plurality of first perifusate receptacles 108, for example, may be pressurized to a common first pressure, and a plurality of second perifusate receptacles 112, for example, may be pressurized to a common second pressure, wherein the first pressure is different than the second pressure. This differential pressure may cause perifusate material to flow from each of the first perifusate receptacles 108 to corresponding ones of the second perifusate receptacles 112, or vice versa. The perifusate reservoir 102 may be arranged in this way so that a plurality of test channels can operate concurrently with a single pressure scheme that shares any one or more of a single gas supply, a single valve, a single pressure regulation means, a single pressurization control system, and the like.

In various embodiments, one or more receptacles of the perifusate reservoir 102 are dedicated to each microperifusion channel 104A. In the prototype embodiment of FIG. 2, for example, a microperifusion chamber 204 is arranged with eight microperifusion channels 204A-204H, and a corresponding perifusate reservoir 202 is arranged with 16 perifusate receptacles. In the prototype of FIG. 2, each of the eight microperifusion channels 204A-204H will have two dedicated perifusate receptacles. In addition to each receptacle being separately pressurized, the perifusate reservoir may be further arranged with gaskets that isolate each pair of perifusate receptacles, which are dedicated to one microperifusion channel, from other pairs of perifusate receptacles, which are dedicated, respectively, to the other channels of the microperifusion chamber 204. In this way, the flow of a first perifusate (e.g., a test perifusate) from a first receptacle and the flow of a second perifusate (e.g., a control perifusate) from a second receptacle into the microperifusion channel can be finely and independently controlled without affecting or being influenced by the operations of other microperifusion channels.

Turning back to FIG. 1, the perifusate reservoir 102 comprises a plurality of conduits arranged to pass perifusate material. Passage of the perifusate material is controlled by pressurizing the environment in and around the various receptacles of the perifusate reservoir 102.

In FIG. 1, a first conduit 118 has a first end 118A oriented at or near the gravitational "bottom" of the first perifusate receptacle 108. The gravitational bottom is the lowest point of the receptacle where fluid would naturally gather under influence of earthly gravity sufficient to overcome any other force on the fluid when a test cycle is in operation. The first conduit 118 has a second end 118B oriented in the second perifusate receptacle 112. The second end 118B is arranged in at least some cases in the space "above" the second perifusate material. In this way perifusate material from the first receptacle 108 can flow (e.g., drop, pour, spray, stream, fall, and the like) into the second receptacle 112.

In at least some cases, the first conduit 118 may include a first interim conduit 120A portion (i.e., a transfer channel). The first interim conduit 120A portion may be a separate and distinct conduit (See, for example, the transfer channel 220A-220H in FIG. 2), or the first interim conduit 120A may be a portion of the first conduit 118. The first interim portion 120A may be, for example, a conduit formed (e.g., bored, drilled, tunneled, hollowed, formed via a printing process, or the like) through the perifusate chamber 104.

A second conduit 122 in FIG. 1, has a first end 122A oriented at or near the gravitational bottom of the second perifusate receptacle 112 and a second end 122B oriented at or near the entry point of respective microperifusion channel 104A. In at least some cases, the second conduit 122 may include a second interim conduit 120B portion. The second interim conduit 120B portion may be a separate and distinct conduit, or the second interim conduit 120B may be a portion of the second conduit 122. The second interim conduit 120B may be, for example, a conduit formed (e.g., bored, drilled, tunneled, hollowed, formed via a printing process, or the like) through the perifusate chamber 104.

In the systems described in the present disclosure, the perifusate reservoir will have at least one pressure port by which one or more perifusate receptacles can be put under pressure. The pressure will directionally drive or draw perifusate material into one or more microperifusion channels.

In more detail, the perifusate reservoir 102 in FIG. 1 has a plurality of pressure ports including a source pressure port 124 and a transfer pressure port 126. A gas, such as air (e.g., 5% $CO_2$ and balance ambient air, or some other physiologic gas) may be pumped into one or more of the pressure ports 124, 126. One or more valves (FIG. 7) may be fully or partially opened and closed to selectively control pressure in any one or more of the plurality of perifusate receptacles. In this way, the flow of perifusate material between receptacles and to one or more microperifusion channels can be finely controlled.

In at least one embodiment, the first conduit 118 arranged to pass perifusate material 110 between a first receptacle 108 and a second receptacle 112 is a "low-resistance" transfer tube, and the second conduit 122 arranged to pass perifusate material 114 from the second receptacle 112 to the microperifusion channel 104A is a "high-resistance" source tube. In this case, low-resistance and high-resistance are terms used to denote the relative resistance of fluid flow in one conduit relative to another conduit. Hence, it is understood by one of skill in the art that fluid will flow more easily in a "low-resistance" transfer tube (e.g., a first conduit 118) than fluid will flow in a "high-resistance" source tube (e.g., a second conduit 122). In some cases, the resistance to fluid flow is based on an inside diameter of the conduit. In these or other cases, resistance to fluid flow is based on the material used to construct the conduit.

Considering the prototype embodiment of FIG. 2, and at least some other exemplary embodiments, one or all of the conduits are formed from a biocompatible material having strong mechanical integrity (e.g., resistance to breakage under stress, resistance to thermal degradation, and the like) and strong chemical integrity (e.g., resistance to absorption of chemicals, resistance to molecular breakdown in the presence of many chemicals, and the like) such as poly ether ether ketone (PEEK) tubing. Other materials are also contemplated.

In at least one case, the first conduit 118 has an outside diameter of 0.625 inches (1/16 in.) and an inside diameter of 0.020 inches (1/50 in.). In at least one case, the second conduit 122 has an outside diameter of 0.625 inches (1/16 in.) and an inside diameter of 0.010 inches (1/50 in.), 0.007 inches, 0.005 inches, or some other inside diameter that is smaller than the inside diameter of the first conduit 118. As evident in these cases, the first conduit 118 is used to transfer a test compound perifusate 110 from the first perifusate receptacle 108, through the first interim conduit 120A transfer channel in the microperifusion chamber 104, and into the second source perifusate receptacle 112. And the second conduit 122 is used to transfer source perifusate 114 from the second perifusate receptacle 112 into the base of its respective microperifusion channel 104A, driven by pressure in the second perifusate receptacle 112. The inside diameter of the second conduit 122, in cooperation with the pressure in the second perifusate receptacle 112, contribute to a finely controlled and controllable determination of the rate of flow into the respective microperifusion channel 104A.

The microperifusion channel 104A of FIG. 1 is arranged as a vertical tube having a frit 130, a tissue or cell sample 132, and an oxygen-sensitive dye 134 located therein. In some cases, the microperifusion channel 104A has an inside diameter of about 1.5 mm.

Prior to executing a test cycle, the tissue or cell sample 132 is arranged on the frit 130. The frit 130 in some cases is a polymer frit made of ultra high molecular weight polyethylene (UHMWPE). Other materials for the frit 130 are contemplated. The frit 130 may have any desirable dimension, but in at least some cases, the frit 130 has a diameter and shape that cooperates with the inside size and shape of the microperifusion channel 104A. In at least some cases, the frit 130 has a porosity of 20 micrometers (20 μm), though other porosities are contemplated. In operation, the perifusate material flows through the frit 130, which holds the tissue that is continuously bathed in perifusate material (e.g., fluid) supplied from the receptacles of the perifusate reservoir 102.

The tissue or cell sample 132 (e.g., liver slices, isolated pancreatic islets, or any other biological material) may be arranged on the frit 130 as a mass of cultured cells. The mass can have any desired size suitable for the test of interest. Generally, the size of the tissue or cell sample 132 is selected based on how long the test cycle will run (e.g., minutes, hours, days, or some other duration) in cooperation with the flow rate of perifusate material. Accordingly, toxicity, efficacy, or other effects that occur over any time duration may be observed and tested.

After the perifusate material passes the tissue or cell sample 132, the fluid continues flowing in the microperifusion channel 104A past an oxygen-sensitive dye 134. In some cases, the oxygen-sensitive dye 134 is applied to (e.g., "painted on") glass beads. In other cases, the oxygen-sensitive dye 134 is applied to the inner column surface of the microperifusion channel 104A. In still other cases, the oxygen-sensitive dye 134 is applied in another way.

The oxygen-sensitive dye 134 cooperates with opto-electric sensors 128 to measure or otherwise generate a signal that represents a phosphorescent decay rate of the oxygen-sensitive dye 134. And the phosphorescent decay rate is indicative of the oxygen consumption rate (OCR) of the tissue or cell sample 132 under test. Stated differently, the OCR is the rate at which the tissue or cell sample 132 absorbs oxygen from the perifusate material flowing through the tissue or cells. Hence, the OCR is an integrated measure of energy generation that reflects changes in cell number, viability, and energy utilizing cellular processes. OCR may, for example, be measured as the decrement in oxygen concentration (i.e., partial pressure of oxygen, pO2, or $pO_2$) times the flow rate of perifusate material flowing through the tissue or cell sample 132.

After the perifusate material passes the dye material 134, the effluent perifusate material will exit the microperifusion channel 104A as outflow 136 from a distal portion 138 of the microperifusion channel 104A. The distal portion 138 may be used to load any one or more of the frit 130, the tissue or cell sample 132, and the oxygen-sensitive dye 134 prior to commencing a test cycle. In at least one case, one or more opto-electric sensors 128 are disposably integrated with the microperifusion channel 104A, and in these cases, the one or more sensors 128 may be loaded or otherwise arranged via or about the distal portion 138.

Figure 7:
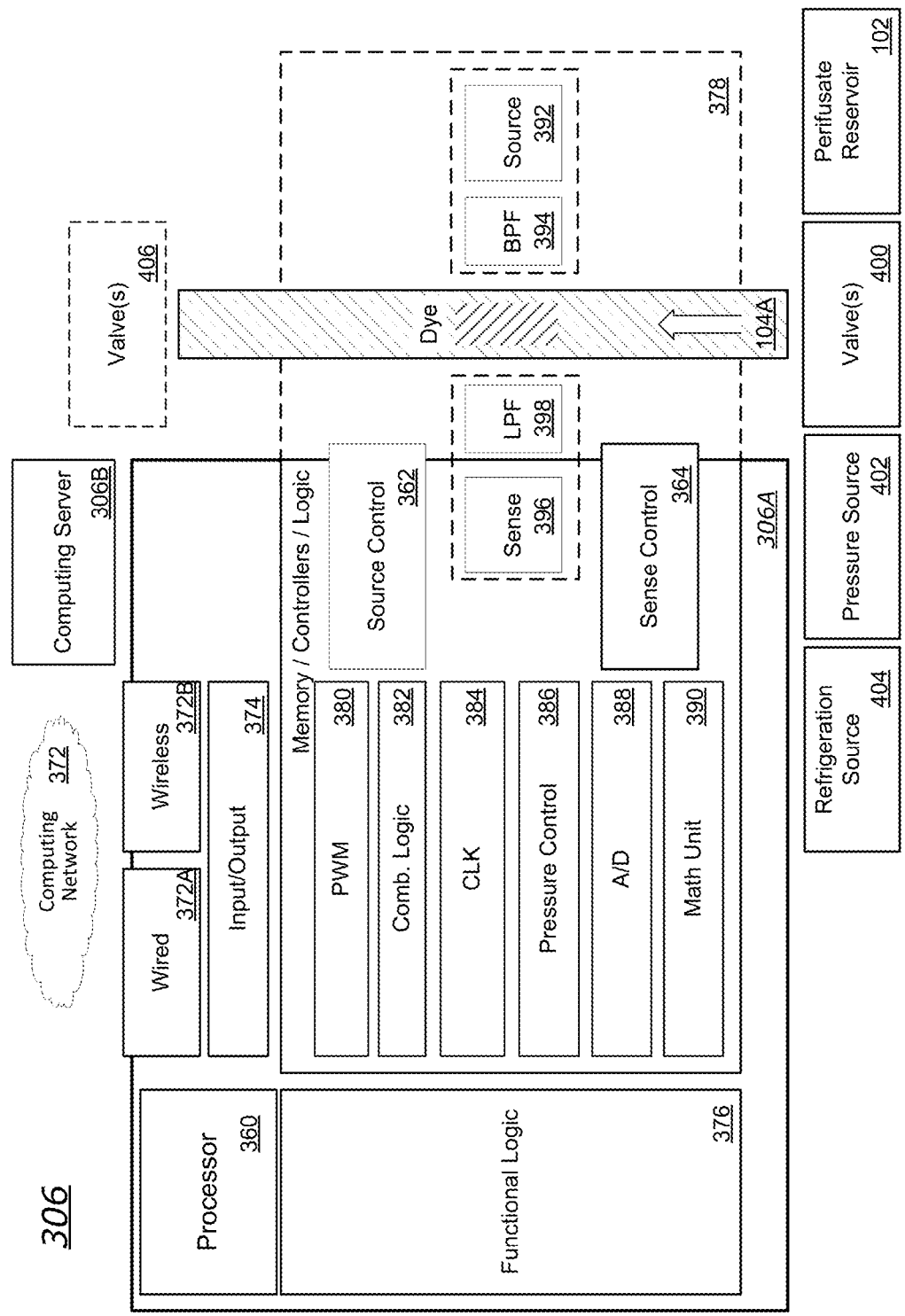
FIG. 7 is an embodiment of the control system of FIG. 6 in more detail.

In some optional embodiments, the rate of outflow 136, and thus the rate of perifusate flow in the microperifusion channel 104A, may be at least partially controlled by the distal portion 138 of the microperifusion channel 104A. The distal portion 138 may, for example, be arranged as an optionally narrowed portion of the microperifusion channel 104A. In addition, or in the alternative, the distal portion 138 of the microperifusion channel 104A may include an optional valve (FIG. 7). In this way, the distal portion 138 may contribute to the fine control of the rate of flow of the perifusate material in the microperifusion channel 104A, and the distal portion 138 may further contribute to maintaining the microperifusion channel 104A as "full" of perifusate material even when the microperifusion channel 104A is not oriented vertically.

The outflow 136 discharges effluent (e.g., "used") perifusate material at the exit (e.g., top) of the microperifusion channel 104A. Samples of the effluent perifusate can be collected for off-line biochemical assay. In some cases, for example, the effluent may be analyzed to measure insulin release rate, lactate production, or some other property indicative of the reaction of the tissue sample to the perifusate material. Accordingly, the systems, devices, and methods of the present disclosure can combine conventional chemical and radio-immunological assays with OCR made possible via substantially transparent microperifusion channels 104A to generate a powerful index of cellular health and function.

The microperifusion channel 104A in the present disclosure is distinguished from known glass-tube perfusion channels. The microperifusion channel 104A is, for example, filled with a flowing perifusate driven by pressure rather than a peristaltic pump. Accordingly, the flow of perifusate in the microperifusion channel 104A is smooth and not pulsing. The pressurized flow in the microperifusion channels of the present disclosure provide for uniform perifusate distribution, which more closely emulates the flow of blood in a living body. Additionally, while the microperifusion channel 104A of FIG. 1 is vertically mounted, this is no longer a requirement because in at least some embodiments, constant pressure maintained in the microperifusion channel 104A creates an environment where perifusate flows continually at a constant rate in a single direction regardless of the orientation of the channel.

Turning to FIG. 2, in at least one example, the multi-channel, multi-receptacle perifusate reservoir 202 is associated with a pressure regulation means such as a single pressure regulator 150, as show in FIG. 1. The pressure regulation means may be integrated with the multi-channel, multi-receptacle perifusate reservoir 202, or the regulation means may be separate and distinct and coupled to the multi-channel, multi-receptacle perifusate reservoir 202. In FIG. 2, a source pressure port 224 and a transfer pressure port 226 are represented.

Considering at least one method of use of the system of FIG. 2, a "control" perifusate material is placed in a set of first perifusate receptacles (e.g., first glass test tubes), and a set of "test" perifusate materials such as a drug-containing perifusate are placed in a second set of perifusate receptacles (e.g., second glass test tubes). Since the system of FIG. 2 includes eight channels, there are eight first perifusate receptacles partially or completely filled with the control perifusate material, and each of the eight second perifusate receptacles is partially or completely filled with a different test perifusate material. The different test perifusate materials may be different concentrations of the same drug, different drugs, different combinations of drugs, or any other differences. It is recognized that in some other cases, each of the eight second perifusate receptacles may be partially or completely filled with a same test perifusate material in order to test or calibrate the system.

Contemporaneous with preparing the first and second sets of perifusate receptacles with control and test perifusate materials, respectively, tissue samples may also be arranged on frits in each of the eight microperifusion channels. It is not required that each of the tissue samples be the same or generally the same, but in the embodiment under discussion, each of the tissue samples is from a common source.

After the perifusion receptacles are suitably filled, and after the microperifusion channels are arranged with suitable tissue samples, the microperifusion chamber and the perifusate reservoir are coupled together. The coupling forms an air tight seal from the outside environment. One or more of the perifusate receptacles are also sealed from each other as described herein. In the present embodiment being described, each of the receptacles is sealed in a way that the receptacle can be a separately pressurized compartment of the perifusate reservoir 202.

As described herein, a test cycle is started by pressurizing each of the first and second perifusate receptacles (i.e., the source reservoirs) to cause the conduits to fill with the control perifusate material. The control perifusate material will flow at a finely controllable rate through each respective microperifusion chamber thereby bathing each respective tissue sample with the flowing control perifusate material. The system may be maintained at the selected pressure for a control period, which may last any selected number of seconds, minutes, or longer. The control period permits the system to reach a "baseline" state after which one or more specific tests or test cycles can be executed.

After the control period ends, pressure in the first perifusate receptacles (i.e., the test material reservoirs) is increased. The increase in pressure in the first perifusate receptacles causes the test perifusate material (e.g., the drug-containing perifusate) to be driven through the first conduit, across the interim conduit (i.e., a transfer channel), and into the second perifusate receptacle thereby "doping" the control perifusate material with the test compound perifusate material. The now-doped perifusate material is driven through the second conduit into the respective microperifusion channel at a finely controllable flow rate. While the perifusate material is flowing across the tissue samples in each channel, OCR measurements can be taken and effluent material can be further assayed in known ways.

Returning to consideration of the microperifusion system prototype of FIG. 2, several test cases are now considered. The test cases illustrate a subset of the operational embodiments that can be constructed and performed by the microperifusion systems, devices, and methods described in the present disclosure. Each of these test cases related to rat liver and rat pancreatic islet testing has been performed by the inventors. Each of the materials, flow rates, substances, sizes, and the like described in association with the prototype has been implemented or considered for implementation in the prototype by the inventors unless expressly stated otherwise. As recognized by one of skill in the art, other materials, flow rates, substances, sizes, and the like, as expressly and impliedly described in the present disclosure, have also been contemplated.

In the prototype of FIG. 2, the inventors fabricated a "plumbing" schema using three-dimensional (3D) stereolithography to "print" eight (8) microperifusion channels into a single perifusion chamber module that includes a plurality of gasketed insertion points for high-resistance and low-resistance conduits (e.g., PEEK tubes) and a perifusate transfer channel. In the prototype of FIG. 2, the perifusate transfer channel is $1/16$ inch diameter, but other diameters are contemplated. In FIG. 2, the perifusate transfer channel has a generally circular cross section (i.e., the perifusate transfer channel is generally tubular), but other cross-sectional shapes are contemplated.

In the case of the prototype represented in FIG. 2, the perifusion chamber module was designed with AUTODESK INVENTOR PRO 2015 software and rendered by PROTO LABS, INC. stereolithography in 0.004 inch layers using a biocompatible (ISO 10993) transparent polymer (WATERSHED XC 11122).

In the case of the prototype represented in FIG. 2, the perifusate reservoir module was machined from clear acrylic plastic. The perifusate reservoir module was further formed with a $1/16$ inch SILASTIC gasket (GE PREMIUM SILICONE II GASKET AND SEAL) to seal and isolate each perifusate receptacle from other perifusate receptacles in the perifusate reservoir chambers when the receptacles are pressurized. And the perifusate reservoir module was also formed with separate ports for pressurizing each perifusate receptacle chamber with ambient air, oxygen ($O_2$), carbon dioxide ($CO_2$), nitrogen ($N_2$), or some other a biocompatible gas or gas mixture that would overlie the perifusate material in each respective perifusate receptacle. When in operation, the sixteen perifusate receptacles (i.e., eight (8) test perifusate test tubes and eight (8) control perifusate test tubes) were pressurized to a level of between about 0.5 pounds per square inch and about 2.5 pounds per square inch (≈0.5-≈2.5 psi).

In at least one round of testing, Krebs Ringer bicarbonate (KRB) solution containing 0.1% bovine serum albumin (BSA), and 25 millimolar (25 mM) sodium bicarbonate was used for islet perifusion analyses, prepared as known by those of skill in the art. For liver perifusion analyses performed in the prototype of FIG. 2, WILLIAMS' E MEDIA (SIGMA-ALDRICH) supplemented with 10% heat-inactivated fetal bovine serum (ATLANTA BIOLOGICALS), two millimolar (2 mM) glutamine, one percent penicillin-streptomycin (1% Pen/strep) and twenty millimolar (20 mM) HEPES (RESEARCH ORGANICS) was used. Glucose, potassium cyanide (KCN), and acetaminophen were purchased from SIGMA-ALDRICH.

In at least one round of testing performed in the prototype of FIG. 2, islets were harvested from SPRAGUE-DAWLEY male rats weighing about 250 grams (g) from CHARLES RIVER were anesthetized by intraperitoneal injection of about 35 milligrams (mg) sodium pentobarbital per 230 g rat. All procedures were approved by the UNIVERSITY OF WASHINGTON INSTITUTIONAL ANIMAL CARE AND USE COMMITTEE and all experiments were performed in accordance with relevant guidelines and regulations. Islets were prepared and purified as known to those of skill in the art and then cultured at 37 degrees Celsius (° C.) in ROSWELL PARK MEMORIAL INSTITUTE (RPMI) MEDIA 1640 (SIGMA-ALDRICH) supplemented with 10% fetal bovine serum for 18 hours prior to the experiments.

In at least one round of testing to prepare tissue samples for used in the prototype of FIG. 2, all procedures were performed under aseptic conditions in a laminar flow hood. After anesthesia was induced in the rats, the midsection was opened up to expose the liver. A piece of liver lobe sized to about four cubic centimeters (≈4 cm$^3$) was removed with surgical scissors. The piece was laid out on a petri dish containing WILLIAMS' E MEDIA (SIGMA-ALDRICH), and after cutting away a layer of capsule, multiple slices were diced with a scalpel; each slice being about one quarter millimeter by one millimeter (≈0.25 mm×1 mm); each slice having a mass of about one to two milligrams (≈1 mg-≈2 mg). Two slices were arranged in each microperifusion channel prior to commencing a test cycle. Upon completion of a test cycle, the remaining liver slices were collected from the respective microperifusion channel and weighed. Oxygen consumption rate (OCR) measurements were normalized to this mass.

In at least one round of testing performed in the prototype of FIG. 2, oxygen tension in the outflow of each tissue microperifusion channel was measured as described herein. While the oxygen-sensitive dye could have been arranged (e.g., "painted") on the inside of the microperifusion channel, in these cases glass beads were used instead. The glass beads from SIGMA-ALDRICH were sized at about 710-1180 microns. The glass beads coated with the oxygen-sensitive dye were layered on top of the tissue sample in the microperifusion channel. The glass beads were coated with the oxygen-sensitive dye by submerging the beads in a 100 mL solution of dichloromethane containing 5 g dimethylsiloxane-bisphenol A-polycarbonate block copolymer from GENERAL ELECTRIC and 25 mg of platinum porphyrin from PORPHYRIN PRODUCTS. The coated glass beads were baked for up to twelve hours at greater than 100° C. in an oven (Model 1310, VWR) and the resulting dried crystals were pulverized with a metal spatula. In another configuration the oxygen-sensitive dye was loaded into gas permeable polystyrene beads and also onto plastic strips.

In at least one round of testing performed in the prototype of FIG. 2, oxygen-sensitive dye excitation and detection of emitted light from the dye was done via optical fibers. At least one optical fiber carried light from a light emitting diode (LED) emitting light at a wavelength of 405 nanometers (nm); and at least one optical fiber returned emitted light to a spectrometer (MFPF-100 multifrequency phase fluorometer lifetime measurement system from TAU THETA) as described herein. The oxygen-sensitive dye was calibrated by the use of an artificial lung that allowed for rapid changes in oxygen content to be accomplished as known to those of skill in the art, and the slope of the signal was 2.2 usec lifetime/(35 nmol O2/ml). Rather than continuously measuring the inflow concentration of oxygen, the inventors have determined the inflow concentration of oxygen by temporarily altering the flow rate; doubling the flow rate, for example, and calculating the inflow oxygen concentration using for each two flow rates (FR) in Equation 1 and then solving the resulting two equations for $O_2\_in$.

$$OCR \approx FR(O_2\_in - O_2\_out) \qquad \text{Eq. 1}$$

In at least one round of testing performed in the prototype of FIG. 2, fractions were collected by use of a FOXY R2 (TELEDYNE ISCO, INC) to collect perifusate outflow into a 96-well plate. Flow rate was calculated by weighing the contents of each well and then dividing the measured mass by the time interval of collection. Insulin in the perifusate outflow fractions was measured using a radioimmunoassay (RIA) kit from LINCO RESEARCH, INC. Trypan blue concentration in the perifusate outflow was measured by absorption at 604 nm in a SYNERGY 4 MICROPLATE READER from BIOTEK INSTRUMENTS, INC.

In at least one round of testing performed in the prototype of FIG. 2, eight (8) pairs of 13 mm×100 mm perifusate receptacle (e.g., test tubes), each having a volume of nine milliliters (9 mL), are inserted into the perifusate reservoir 202. Each perifusate receptacle is partially or completely filled with a test perifusate or a control perifusate. Eight high-resistance (i.e., small-bore) conduits (i.e., flow tubes) and eight low-resistance (i.e., large-bore) conduits (i.e., flow tubes), each about one hundred millimeters (≈100 mm) in length, are inserted into gasketed ports at the base of the microperifusion chamber 204. A shorter, large-bore conduit 236A-236H (i.e., transfer tube) is inserted to complete the perifusate transfer path by which test compound perifusate materials are transferred from a first respective perifusate receptacle (i.e., a test compound test tube) to a second respective perifusate receptacle (i.e., a control compound test tube) where the two perifusate materials combine to form the desired experimental concentration in the second respective receptacle (i.e., the control compound (source) test tube).

The inserted gaskets are cut or otherwise formed from PHARMED BPT TUBING from COLE-PARMER INSTRUMENT COMPANY.

In at least one round of testing performed in the prototype of FIG. 2, temperature of the system is controlled. In this case, an immersion circulator/heater, Model 1122S from VWR, having a thermostat is utilized. Temperature is regulated a plexiglass box measuring about 17 inches long by 17 inches wide by 13 inches tall (17 in.×17 in.×13 in. (l×w×h)) filled with water. The prototype of FIG. 2 is submerged in the water.

After partially or completely filling the 16 perifusate receptacles, in at least one round of testing performed in the prototype of FIG. 2, the inventors placed the microperifusion chamber 204 module on top of the perifusate reservoir 202 module and sealed the two modules together via a fastening means (e.g., screws). MASTERFLEX L/S 16 tubing from COLE-PARMER INSTRUMENT COMPANY was attached to two source pressure ports on the perifusate reservoir 202 module and secured. The prototype was then partially submerged into the water to a depth that allowed about one inch (≈1 in.) of the top 1 inch of the microperifusion chamber 204 module to protrude from the water. The immersion heater was turned on for about 30 minutes and the system was observed until the water temperature reached about 37° C. The two MASTERFLEX L/S 16 tubes respectively attached to the two source pressure ports of the perifusate reservoir 202 were hooked up to pressure regulators, and the pressure regulators were set to a desire pressure of about 0.5 to 2.5 psi. Both perifusate receptacles of each respective microperifusion channel were purged with a gas of about 5% $CO_2$, balance air, for about five minutes. Next, vent ports were capped, and the microperifusion channels were permitted to fill up with perifusate material. The effluent perifusate material was collected, and the flow rate was confirmed or adjusted as needed by adjusting one or both pressure regulators. Next, rat liver tissue samples as previously described were loaded in to the microperifusion channels of the microperifusion chamber 204, and each sample was given time to settle to the bottom of the respective channel. In cases where islets or cells were used, a porous frit was first inserted into the microperifusion channel and advanced to about one fifth of an inch (0.2 in.) from the bottom of the respective microperifusion channel prior to adding the islets or cells. In cases where a slice of liver was used, the tissue sample was inserted into the microperifusion channel without a frit.

Finally, in at least one round of testing performed in the prototype of FIG. 2, outflow conduits (i.e., tubes) were inserted into the microperifusion channels to allow submersion of the prototype device beneath the surface of the water if desired. In some cases, the effluent perifusate was collected for offline testing. In at least one case, the outflow conduits were formed from high purity perfluoroalkoxy (HPFA) tubing from IDEX HEALTH AND SCIENCE, LLC having an outside diameter of 1/16 inch. For at least some test cycles, sampling of the perifusate material effluent and recording control pO2 levels proceeded for several hours (e.g., two to three hours) to establish a stable baseline. After a stable baseline was established, pressure was changed in one or both perifusate receptacles to cause the transfer of a "test" perifusate material from a first perifusate receptacle (i.e., a test solution test tube) into a second perifusate receptacle (i.e., a control solution test tube) in the perifusate reservoir 202. The pressure change in at least some test cycles included transiently (i.e., for about ten to 15 second) pressurizing the first perifusate receptacle to more than two pounds per square inch (>2 psi). This action caused test perifusate material from the first perifusate receptacle to be injected into the contents of second perifusate receptacle via the interim conduit (i.e., the transfer channel). The perifusate material, which now included the test compound perifusate material and the control substance perifusate material, continued to flow through the respective microperifusion channel where OCR tests and perifusate effluent tests occurred.

Those of skill in the art understand that calculating the increment or decrement of particular substances (e.g., oxygen, hormones, metabolites, and other substances) that are either extracted or released by tissue under test demands that the perifusate flow rate be known and stable. In at least one round of testing performed in the prototype of FIG. 2, the inventors first characterized the control and stability of flow rates and their dependence on perifusate reservoir 202 pressure and conduit resistance for extended periods of time. The inventors then validated the prototype for biological testing tasks by replicating known results showing changes in OCR in response to increased glucose level by a small number of isolated islets, and to the drug acetaminophen by precision-cut slices of rat liver tissue.

The inventors have discovered that finely controllable perifusate flow rates in a plurality of microperifusion channels in the prototype are achievable by changing gas pressure between about 0.5 psi and about 2.5 psi in the perifusate reservoir 202 module. These flow rates can be very low, and the flow rates can be very stable.

Figure 3:
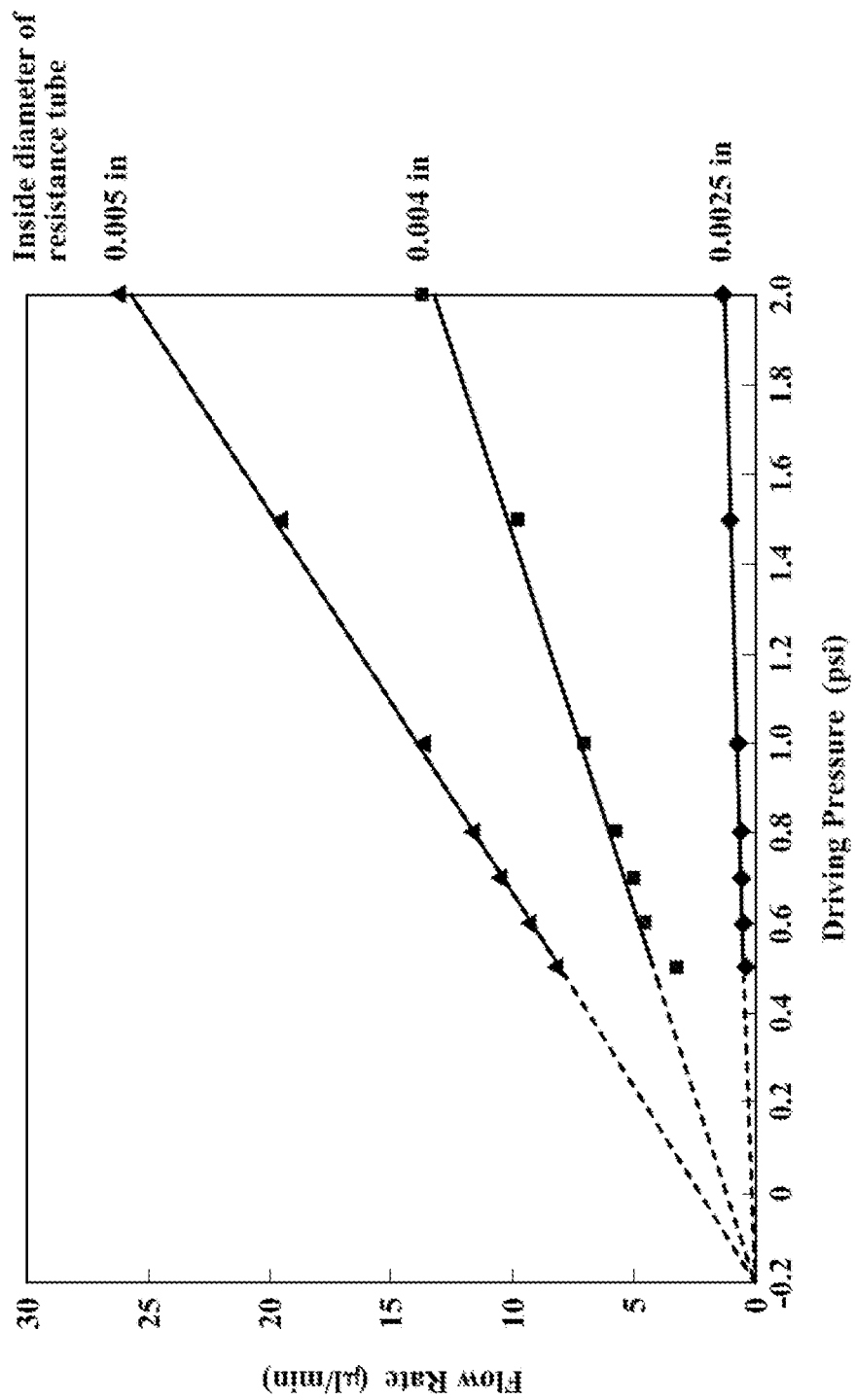
FIG. 3 demonstrates testing performed in the prototype of FIG. 2B using high-resistance conduits (i.e., flow tubes) of various dimensions.

FIG. 3 demonstrates testing performed in the prototype of FIG. 2 using high-resistance conduits (i.e., flow tubes) of various dimensions. In the cases represented in FIG. 3, conduits of PEEK tubing from IDEX HEALTH AND SCIENCE, LLC have an outside diameter of 1/16 inch. Three different structures of high resistance conduits were tested: a first having an inside diameter of 0.0025 inch, a second having an inside diameter of 0.004 inch, and a third having an inside diameter of 0.005 inch. As represented in FIG. 3, linear changes to flow rate in the respective conduit caused by changes in driving pressure are achievable. In this way, the inventors have discovered that a conduit can be selected with various properties associated with resistance (e.g., inside diameter) to produce a desired range of flow rates. A properly selected small-bore conduit contributes such a high resistance to the perifusate flow in the system that the flow resistance from the perifusate reservoir 202 to the microperifusion chamber 202 is determined by the smaller flow conduit (i.e., the conduit from the perifusate reservoir 202 to the microperifusion chamber 202), with little or no contribution from the larger flow conduit (i.e., inside diameter >0.025 in).

In various rounds of testing performed in the prototype of FIG. 2, perifusate material flow was collected and measured at each of several perifusate reservoir 202 pressures from about 0.5 psi to about 2.5 psi. In these tests, the inventors achieved finely controllable flow rates over a flow rate range in the microperifusion channels of less than about one-tenth microliter per minute to about 200 microliters per minute (<≈0.1 µL/min to ≈200 µL/min), which is desirable for practical tissue perifusion tasks. Accordingly, the inventors discovered that microperifusion channel flow rate is linearly related to driving pressure as expected of laminar (i.e., non-turbulent) fluid flow, which depend on the fourth-power of tube diameter as interpolated (the lines) according to the known Hagen-Poiseuille equation. Furthermore, extrapolation of the lines in FIG. 3 toward the origin shows that the intersect at a common, no-flow pressure of about 0.2 psi corresponds exactly to the back-pressure exerted by a 5.5-in column of perifusate fluid reservoir conduits and the top of the microperifusion channel flow columns.

In at least one round of testing performed in the prototype of FIG. 2, perifusate material flow rates were measured before, during, and after the transfer of perifusate material from the first perifusate receptacles (i.e., the test source reservoirs). At the desired time, the pressure in the transfer pressure first receptacle was increased to about 2.5 psi, and the perifusate material completely moved into the second receptacle (i.e., the source test tubes) in the source reservoirs within about 15 seconds. At this time, the test perifusate material pressure regulator was reduced (e.g., shut back off). Taking this action caused no measurable fluctuation in flow rate at the outflow of the respective microperifusion channel.

In at least one round of testing performed in the prototype of FIG. 2, in order to assess the time it took for the tissue sample in the respective microperifusion channel to be exposed to the test perifusate material (i.e., the perifusate material from the first receptacle that is moved into the second receptacle), a trypan blue substance at about 0.008% was added to the first receptacle the concentration of the trypan blue substance in the microperifusion effluent outflow was measured by light absorbance. The actual time taken to reach equilibrium, and the final composition of the outflow after mixing, depends on the initial contents of the both perifusate receptacles. When the volumes in the second receptacle (i.e., the source reservoir) and the volume in the first receptacle (i.e., the transfer reservoir) were equal, about 15 minutes passed until the outflow concentrations reached steady state. The concentration in the outflow at steady state was calculated as the weighted average of the composition with respect to volume. It was discovered that more rapid changes in perifusate media composition could be obtained by transferring a larger amount of perifusate media in the first receptacle (i.e., the transfer reservoir) to a small amount of perifusate media in the second receptacle (i.e., the perifusion reservoir).

Due to the testing performed in the prototype of FIG. 2, the inventors have discovered that a system to assess islet function is expandable to a large number of channels. In such a system, reducing the size of the system also reduces the number of islets required to produce a detectable endpoint. In the case of oxygen consumption rate (OCR) measured as the difference between inflow and outflow oxygen concentration, the detection limit is linked to the number of islets and the perifusate material flow rate. The lower the flow rate, the lower the number of islets required to perform meaningful tests.

Figure 4A:
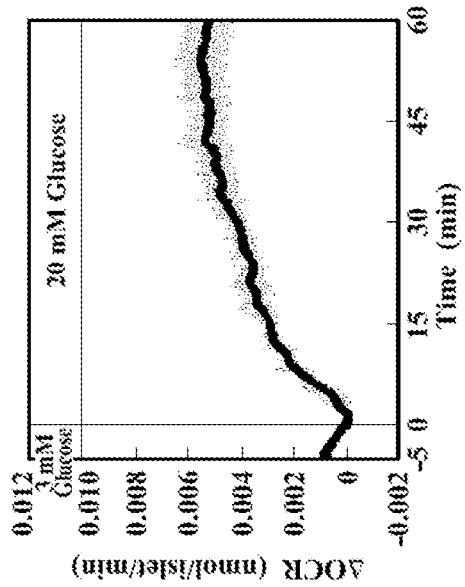
FIG. 4A shows in a graph how islets at 10 per microperifusion channel were perifused at 7 µL/min, and OCR was stable, and the variability was only a few percent of the glucose responses executed with the prototype of FIG. 2B.
Figure 4B:
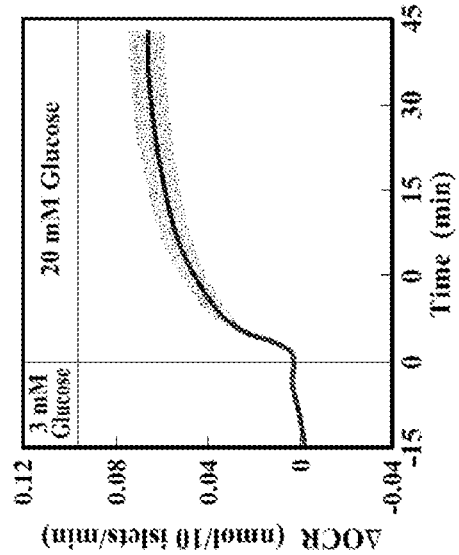
FIG. 4B shows in a graph glucose responses from only 1 islet at a flow rate of 1.5 µL/min executed with the prototype of FIG. 2B.
Figure 4C:
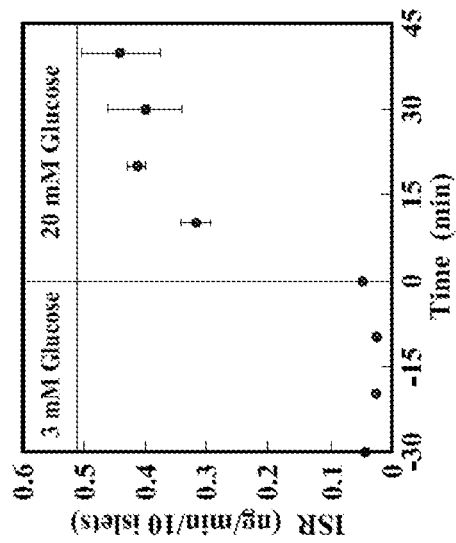
FIG. 4C shows outflow fractions collected in three of microperifusion channels and assayed for insulin.

In FIG. 4A, pancreatic islets at 10 per microperifusion channel were perifused at 7 µL/min, and OCR was stable, and the variability was only a few percent of the glucose responses. FIG. 4B shows in a graph glucose responses from particular tests executed with the prototype of FIG. 2B. And FIG. 4C shows outflow fractions collected in three of microperifusion channels and assayed for insulin. In the present disclosure, FIGS. 4A-4C may be collectively referred to as FIG. 4.

As evident in FIG. 4A, the effects of glucose were very similar for all microperifusion channels. At the end of the experiment, the flow rate was doubled by doubling the pressure in the perifusate reservoir 202 two times and the actual OCR was calculated as described herein. Change in OCR=0.63+/−0.082 nmol/100 islets/min in response to 20 mM glucose.

In at least one round of testing performed in the prototype of FIG. 2, outflow fractions were collected and the content of insulin was measured. Both OCR and insulin secretion responses to glucose were consistent with previous, larger scale perifusion systems. To determine if the prototype system of FIG. 2 could resolve glucose responses with very small amounts of tissue, three channels were loaded with only one islet, a flow rate of 1.5 µL/min was selected by using a high resistance conduit having an inside diameter of 0.0025 inch, and a pressure of about 2 psi was applied. In these tests, glucose responses were again well-resolved and similar to results obtained with higher numbers of islets. Although the data was noisier than that obtained with 10 islets, the data was useful to validate the prototype system of FIG. 2. The tests conducted by the inventors demonstrates the ability of the prototype system of FIG. 2 to generate six real time OCR responses with only 60 islets, and even less if only steady state changes are needed.

Figure 5:
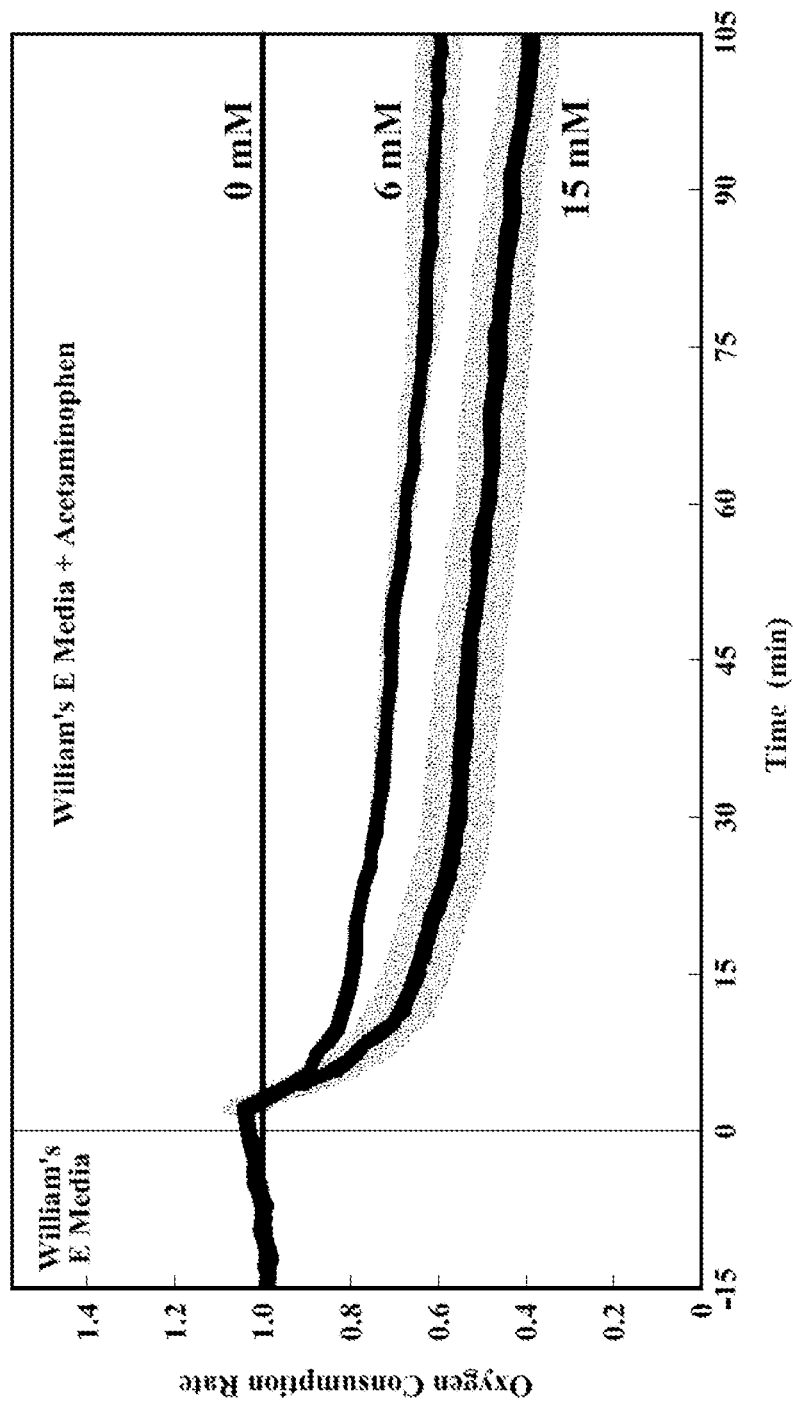
FIG. 5 is a graph illustrating the effect of acetaminophen on liver oxygen consumption in the prototype of FIG. 2B

FIG. 5 is a graph illustrating the effect of acetaminophen on liver oxygen consumption in the prototype of FIG. 2. To support the utility of the prototype to the pharmaceutical industry, the inventors replicated a known characterization of the effects of the drug acetaminophen on liver OCR. Liver slices were cultured for up to twelve hours, and two 1 mg liver slices were arranged as tissue samples in eight (8) microperifusion channels of the microperifusion chamber 204. The tissue samples were then microperifused for about three hours in control perifusate material to measure baseline OCR. The inventors then switched six microperifusion channels to one of two acetaminophen-containing perifusates (i.e., two (2) concentrations in triplicate). By executing this test cycle, the inventors were able to demonstrate the reproducibility of OCR inhibition as shown in FIG. 5. Here, OCR in the two microperifusion channels that were not exposed to acetaminophen remained flat. Conversely, in the microperifusion channels exposed to acetaminophen, the OCR was lowered 40 percent (40%) and 60 percent (60%) due to the 6 mM and 15 mM acetaminophen concentrations. These results were similar to results obtained in known studies performed using large, peristaltic pump-driven perifusion systems.

As evidenced in the foregoing description associated with FIGS. 1 to 5, the inventors have demonstrated systems, devices, and methods of a novel and non-obvious microperifusion system that enables live tissue test cycles of minutes, hours, and even days. The inventors illustrated the use of the prototype system by measuring oxygen consumption rates (OCR) using highly sensitive sensors, but the inventors have also contemplated other sensors and assay protocols can also be used. Whereas the inventors demonstrated optical detection of OCR, it has also been contemplated that optical phosphorescent measurements of the cell or tissue can be performed to directly assay cellular NAD (P)H and calcium as well as genetically expressed sensors for $H_2O_2$ and ATP. Furthermore, the inventors have contemplated an adaptation their microperifusion system to the practical implementation of a perifusate fraction collector method by which hormones, metabolites, and signaling molecules can be measured concurrently with the optical methods described herein.

In FIGS. 1 to 5 and the associated description, the inventors have also demonstrated a novel and non-obvious flow-through tissue perifusion invention that is scalable for high-throughput, multi-channel operation in the physiological and pharmaceutical industries. The microperifusion system described herein permits very small tissue samples to be perifused at very low flow rates via replacing peristaltic pumps with increments of gas pressure in perifusate receptacles. The embodiment of FIG. 2 was implemented using 3D solid printing fabrication, but other techniques may also be employed to create the perifusate reservoir 202 and microperifusion chamber 204 represented herein. It is recognized by the inventors that systems, devices, and methods implemented in accordance with the present disclosure can be deployed and used in a broad range of laboratory settings that require low- or high-throughput testing of tissues exposed to physiological, pharmacological and toxicological substances and application in personalized medicine.

Having first designed systems, devices, and methods that provide the technical advantages and benefits of the modular perifusate reservoirs 102, 202 and microperifusion chambers 104, 204 illustrated in FIGS. 1-5 and described in the associated paragraphs, the inventors further recognized that an innovative control system module was an important aspect of the invention that would permit the systems to scale more easily, efficiently, and effectively.

Figure 6:
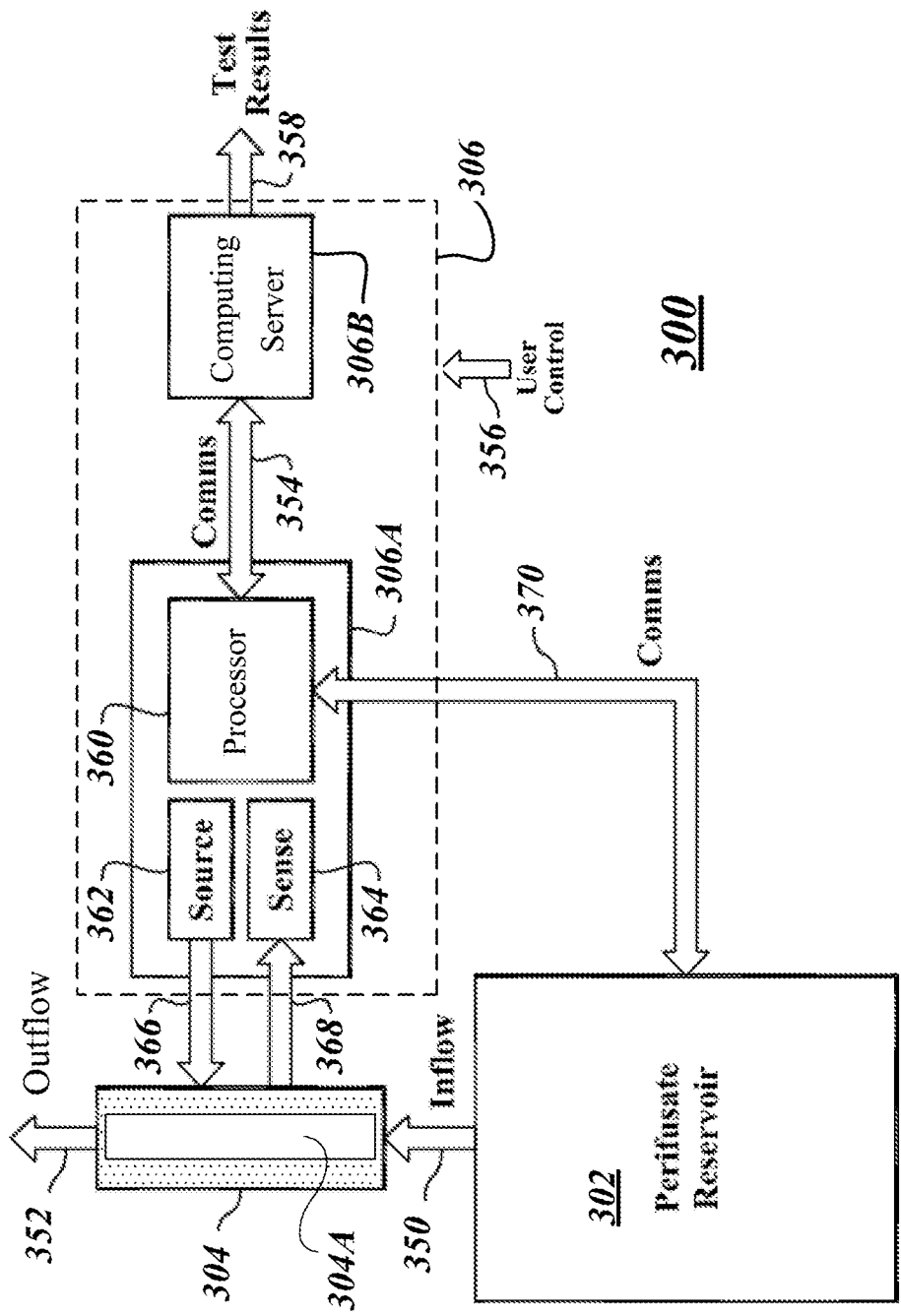
FIG. 6 is an embodiment of a pressure-driven, adjustable throughput fluidics pressure-driven, adjustable throughput fluidics system 100 for performing tissue or cell perifusions.

FIG. 6 is an embodiment of a pressure-driven, adjustable throughput fluidics (pressure-driven, adjustable throughput fluidics) system 300 for performing tissue or cell perifusions. The pressure-driven, adjustable throughput fluidics system 300 is arranged to monitor the oxygen consumption rate (OCR) of tissue samples perifused at finely controllable flow rates through each of a plurality of perifusion channels. In some cases, the tissue samples are sized on the order of one microgram (1 μg), 10 μg, 50 μg, 750 μg, or some other quantity.

The pressure-driven, adjustable throughput fluidics system 300 of FIG. 6 may be described by way of three functional components: a perifusate reservoir 302, a microperifusion chamber 304, and an advanced control system 306. The components may be formed as modules that are temporarily or fixedly coupleable together. The modular design permits a scientific practitioner to selectably scale the pressure-driven, adjustable throughput fluidics system 300 in a way that accommodates as many or as few separate and distinct perifusate channels as desired.

The perifusate reservoir 302 is along the lines of the perifusate reservoir 102 of FIG. 1 and the perifusate reservoir 202 of FIG. 2. The microperifusion chamber 304 is along the lines of the microperifusion chamber 104 of FIG. 1 and the microperifusion chamber 204 of FIG. 2, and the microperifusion channel 304A is along the lines of the microperifusion channel 104A of FIG. 1 and the microperifusion channels 204A-204H of FIG. 2. It is recognized by one of skill in the art that a detailed illustration and a repetitive description of the perifusate reservoir 302, the microperifusion chamber 304, and the microperifusion channel 304A is omitted here to avoid unnecessarily clouding or crowding the particular discussion related to the control system module 306 of FIG. 3.

The perifusate reservoir 302, in some embodiments, comprises a plurality of pairs (e.g., 2 pairs, 4 pairs, 8 pairs, 64 pair, 96 pairs, or some other number of pair) of reservoir vessels. The vessels may be independent tubes (e.g., test tubes), cylinders, flasks, bottles, or some other container in some embodiments, or the reservoir vessels may be integrated into the perifusate reservoir 302 in other embodiments. The reservoir vessels may be disposable, sterilizable, machine washable, hand washable, or formed in another way. Each reservoir vessel may be independent. Alternatively, or in addition, a plurality of vessels may be configured together as a single unit.

In some embodiments, a perifusate is supplied (e.g., poured, filled, injected, squirted, dripped, or the like) into various ones, or all, of the reservoir vessels. The perifusate may be supplied into the reservoir vessels prior to, during, or prior to and during a test cycle. In at least one embodiment, one reservoir vessel of a pair is provided with a control perifusate, and the other reservoir vessel of the pair is provided with a test perifusate. By pressurizing the air or other medium in the perifusate reservoir 302 (e.g., to about one pound-per-square inch (1 psi) or to a different pressure), the perifusate in one or more of the reservoir vessels is driven upward into and through each vertical channel in the microperifusion chamber 304.

In the pressure-driven, adjustable throughput fluidics system 300 of FIG. 6, the microperifusion chamber 304 is illustrated "above" the perifusate reservoir 302. In addition, the perifusate in the reservoir vessels is described as being driven "upward." In at least one embodiment, channels of a microperifusion chamber 304 are arranged in a substantially vertical orientation. In at least one embodiment, a perifusate reservoir 302 is oriented gravitationally below the microperifusion chamber 304. Other arrangements are contemplated, however. For example, surface tension, surface friction, adhesion, the sizes of conduits where perifusate traverses, and other principles permit pressure (e.g., gas pressure, mechanical pressure, hydraulic pressure, or the like) of any type to advance, withdraw, or bias the flow of perifusate in a direction selected by the scientific practitioner. Accordingly, various embodiments of the present disclosure and the claims that follow are not implicitly or inherently limited to any particular orientation unless the context expressly dictates such an orientation.

In some cases, the perifusion is performed at the finely controllable low flow rate of 10 microliters per minute (10 μL/m), 50 μL/m, 100 μL/m, 250 μL, or some other rate. The selected finely controllable flow rate is delivered with acceptable accuracy, such as within about ten percent (≈10%) of the selected flow rate, by a reservoir valve (e.g., ball valve, gate valve, butterfly valve, needle valve, or another type of valve means). The reservoir valve may be integrally formed with the perifusate reservoir 302 in some embodiments. Alternatively, the reservoir valve may be separately formed and coupleable or coupled to the perifusate reservoir 302. In some cases, the reservoir valve is controlled or otherwise controllable via the control system 306 of the pressure-driven, adjustable throughput fluidics system 300.

The finely controllable flow rate in some cases is manually set by a user (i.e., a scientific practitioner) of the pressure-driven, adjustable throughput fluidics system 300. Manual control by the user to set a finely controllable flow rate may be performed using a mechanical reservoir valve in some cases, using a controllable electro-mechanical reservoir valve coupled to a controller (e.g., a computing device) in some cases, or by another means. Alternatively, the finely controllable flow rate may be set automatically by an algorithm, a formula, a software program, or by some other means associated with a computing device of the control system 106; the computing device being coupled to an electronic controllable reservoir valve when in operation. In some cases, the reservoir valve includes, or is otherwise associated with, a gas pressure regulation device (i.e., a regulator, an expansion reservoir, or some other regulating means).

The microperifusion chamber 304 in some embodiments is modularly coupled to the perifusate reservoir 302 when in operation. The modular coupling may form or temporary or fixed bond that is a sealed bond. The sealed bond permits perifusate from the perifusate reservoir 302 to be driven under pressure through one or more of a plurality of perifusate channels at a perifusate material inflow interface 350.

The number of channels in the plurality of perifusate channels may be the same in some embodiments and different in other embodiments. For example, embodiments may include two (2) channels, four (4) channels, eight (8) channels, 16 channels, 64 channels, 96 channels, or some other number of channels. In one prototype constructed and tested by the inventors (e.g., FIG. 2), the pressure-driven, adjustable throughput fluidics system included eight (8) channels. The plurality of perifusate channels may be arranged in parallel, in a row, in a column, in an array of rows and columns, in groups, in a cluster, or in any other desirable arrangement.

Each perifusate channel of the microperifusion chamber 304 in some embodiments is arranged to support microgram tissue samples on a porous frit through which physiological, bicarbonate buffers flow at a selected flow rate for a particular test cycle. The selected flow rate may be, for example, about one to two microliters per minute ($\approx$1-2 µL/min). The particular test cycle may operate over seconds, minutes, hours, or days.

Each perifusate channel of the microperifusion chamber 304 in some embodiments is arranged with an oxygen ($O_2$) sensitive, fluorescent porphyrin dye. The $O_2$-sensitive dye is used as a means to continuously measure tissue oxygen-consumption rate (OCR). Continuously measuring OCR may include periodically sampling light passed through, instantiated, or otherwise associated with the $O_2$-sensitive dye. The periodic sampling may occur according to a selectable or a fixed time period.

The perifusate that passes by the tissue samples is effluent that is permitted to pass from the microperifusion chamber 304 at a perifusate material outflow port 352. In some cases, perifusate effluent samples are collected for biochemical assay, radio-immunological assay, or for some other reason.

The control system 306 of the pressure-driven, adjustable throughput fluidics system 300 includes, in at least some embodiments, a first control sub-system (i.e., an electronic logic module 306A) coupled or otherwise coupleable to a second control sub-system (i.e., a remote computing device 306B). The remote computing device 306B may be physically located in proximity to the electronic logic module 306A (e.g., in the same housing, in the same room, in a room on a same campus). Alternatively, the remote computing device 306B may be located far away from the electronic logic module 306A (e.g., in a different, in a different state, in a different country). The remote computing device 306B may in some cases be a distributed computing device (e.g., a "cloud" computing device, a server farm computing device, or the like). Alternatively, the remote computing device 306B may be a local computer (e.g., laptop computer, desktop computer, tablet computer, smart phone, or the like).

The electronic logic module 306A and the remote computing device 306B are communicatively coupled via a first communications link 354. The first communications link 354 may include any suitable communications medium. The first communications link 354 may for example, be a wired link, a wireless link, or a link having both wired and wireless structures (e.g., universal serial bus (USB), Ethernet, BLUETOOTH, on-circuit-board communications bus, or the like). Though not shown in FIG. 6, it is recognized that one or any number of portions of the first communications link 354 may include or otherwise traverse a network such as an intranet or the Internet.

A scientific practitioner may control any number of parameters of the pressure-driven, adjustable throughput fluidics system 300 via a user control port 356. User control port 356 may include any mechanism arranged to couple an input device (e.g., keyboard, mouse, display, touch screen, another computing device (e.g., smartphone, tablet, laptop), dials, switches, and the like) with a computing device such as control system 306. In FIG. 6, user control 356 is illustrated as a means to provide input to the control system 306. It is recognized that the user control 356 may alternatively or additionally include a means to provide direct or indirect input to one or both of the electronic logic module 306A and the remote computing device 306B.

The scientific practitioner and other persons or computing devices may receive output information from an output port 358 of the control system 306. The output port 358 may include any mechanism arranged to couple an output means (e.g., display, speaker, another computing device (e.g., smartphone, tablet, lap, memory device (e.g., flash drive, disk drive), transceiver, or the like) to the control system 306. Along these lines, the output port 358 may facilitate passage of test results, parameter values, or any other data from one or both of the electronic logic module 306A and the remote computing device 306B.

The electronic logic module 306A includes a processor 360. In at least one case, processor 360 is a custom-programmed PIC32MZ microprocessor from MICROCHIP TECHNOLOGY, INC. The processor 360 is arranged to control test cycles (e.g., experimental protocols) of the pressure-driven, adjustable throughput fluidics system 300.

The electronic logic module 306A also includes any number of sensors arranged to capture information regarding a perifusion operation. For example, the sensors may be optically-based, radio frequency (RF) based, audio frequency based (e.g., ultrasound), radiologically based (e.g., gamma-emitters, x-ray, magnetic resonance imaging (MRI)), or based on another physical property of cells, tissue, perifusate, or the like. In FIG. 6, the sensors include source sensor logic 362 and sense sensor logic 364. In at least one embodiment, the source sensor logic 362 includes a light source such as a light emitting diode (LED). In at least one embodiment, the sense sensor logic 364 includes at least one light-sensitive device such as a photoelectric diode (PED). The electronic logic module 306A further includes other logic (e.g., electronic circuits, software) to generate electronic signals, amplify electronic signals, attenuate electronic signals, buffer information, and the like, which logic is not shown to avoid obscuring other relevant structures.

In one embodiment, the remote computing device 306B directs the electronic logic module 306A to perform a perifusion test cycle. The processor 360 of the electronic logic module 306A serially generates, for each perifusion channel of the microperifusion chamber 304 in turn, a direction to the source sensor logic 362 to output a source signal 366 into the respective channel. The source signal 366 may be, for example, an LED pulse that causes a corresponding response signal 368 to be reflected or otherwise communicated back from oxygen-sensitive dye and other material in the respective channel. After the output of the source signal 366, the processor 360 will direct the sense sensor logic 364 to produce an output (e.g., read, measure, generate, perceive, or the like) representative of the response signal 368. The sense sensor logic 364 may, for example, include a photoelectric diode (PED), and the output of the sense sensor logic 364 may be a measurement from the PED. Based on the source signal 366, the material in the perifusion channel of interest may reflect light, generate light, or both reflect and generate. In at least one case, the material in the perifusion channel includes a fluorescent dye material that produces a light signal representative of oxygen in the perifusate material effluent that has passed a cell or tissue sample located in the channel. By way of the source and sense sensors logic 362, 364 and their associated signals, the processor 360 is arranged to capture data generated in the channel.

Processor 360 may be arranged to further control the pressure-driven, adjustable throughput fluidics system 300 via a second communications link 370. The second communications link 370 may include any suitable communications medium. The second communications link 370 may, for example, be a wired link, a wireless link, or a link having both wired and wireless structures (e.g., universal serial bus (USB), Ethernet, BLUETOOTH, on-circuit-board communications bus, or the like). Though not shown in FIG. 6, it is recognized that one or any number of portions of the second communications link 370 may include or otherwise traverse a network such as an intranet or the Internet.

Via the second communications link 370, processor 360 can control any number of valves, pumps, or other mechanisms to provide a finely controlled flow rate of perifusate material into the microperifusion chamber 304. The processor 360, via control information passed on the second communications link 370, may further control which perifusate material (e.g., control material, test material) is passed into the selected channel 304A from the perifusate reservoir 302. The perifusate material passes from the perifusate reservoir 302 into the selected channel 304A of the microperifusion chamber 304 as inflow at the perifusate material inflow interface 350. As the perifusate material passes through a the selected channel 304A of the microperifusion chamber 304, any number of source signals 366 and response signals 368 are produced. The response signals 368 represent changes to tissue or cells in the perifusion channel 304A caused by the perifusate material flowing about and through the sample tissue or cells in the selected channel 304A. After the perifusate material passes the tissue or cells, the perifusate material exits the microperifusion chamber 304 as outflow at the perifusate material outflow port 352. In some cases, the perifusate material exiting the selected channel 304A is maintained in a separate repository (i.e., separated from one or more other microperifusion channels). In other cases, the perifusate material exiting two or more channels of the microperifusion chamber 304A is consolidated in a single repository for disposal. The perifusate material exiting the microperifusion chamber 304 as outflow may be further assayed, disposed of, or used for some other purpose.

In addition to controlling the execution of individual and specific perifusion test cycles, control system 306 is further arranged to perform acts of defining, directing, executing, and controlling experimental protocols, acquiring and analyzing data, displaying outputs, archiving results, and the like. As described in the present disclosure, control system 306 may, for example, process response signals 368 (e.g., by performing acts of analyzing, averaging, calculating, compressing, uploading, and the like), produce test results, and communicate test results to presentation means (e.g., displays, printers, or the like) or other computing devices.

FIG. 7 is an embodiment of the control system 306 of FIG. 6 in more detail. In the embodiment, the electronic logic module 306A is arranged to communicate with the remote computing server 306B via a network 372, and the electronic logic module 306A is arranged to communicate with the perifusate reservoir 302 via network 372. Accordingly, network 372 may include any one or more of a wide area network (e.g., a WAN such as the Internet), a local area network (e.g., a LAN such as implemented via Ethernet), a personal area network (e.g., a PAN such as implemented by USB or BLUETOOTH), or any other suitable network.

First communications link 354 (FIG. 6) and second communications link 370 (FIG. 6) may be implemented in the control system 306 via one or both of a wired communications interface 372A and a wireless communications interface 372B.

An input/output (I/O) means 374 is arranged to pass information into the control system 306 and out from the control system 306. The I/O means 374 may, for example, include general purpose input/output circuits, buffer circuits, latching circuits, interrupt circuits, and other such logic. The I/O means 374 may pass control information such as configuration parameters for specific test cycles, timing information, and the like. The I/O means 374 may pass data information such as the results of particular test cycles captured within the control system 306. In any number of cases, the I/O means 374 may be arranged coupling to any one or more of human input devices (e.g., keyboards, computer mice, touch screens, and the like) presentation devices (e.g., displays, printers, audible sensors, haptic sensors, and the like), computing devices (e.g., smart phones, tablets, wearable computing devices, distributed computing devices, Internet of Things (IoT) devices, and any other type of computing device) and the like.

Functional logic 376 in the electronic logic module 306A is arranged to carry out functional aspects of the electronic logic module 306A. Exemplary, but not limiting, functions include power supply monitoring and control, motion control, watchdog timers, temperature monitoring and control, memory maintenance and backup, and the like. Functional logic 376 may, like other logic in the electronic logic module 306A, operate at the direction of processor 360. In addition, or in the alternative, functional logic 376 may operate autonomously.

A memory/controllers/logic module 378 is arranged as a grouping of memory, circuitry, and other such logic to carry out functions associated with microperifusion test cycles. The memory/controllers/logic module 378 may be considered as the "brain" of a pressure-driven, adjustable throughput fluidics (pressure-driven, adjustable throughput fluidics) system for tissue or cell perifusions. The memory/controllers/logic module 378 includes software instructions executable by processor 360 and electronic circuitry. One or more portions of the memory/controllers/logic module 378 may be totally contained by the electronic logic module 306A, partially contained by the electronic logic module 306A, or associated with, but not physically contained by the electronic logic module 306A. As evident in FIG. 7, and further described herein, portions of the memory/controllers/logic module 378 may be located outside of the physical bounds of the electronic logic module 306A and oriented about a microperifusion channel 104A.

Among other logic, as described herein, the memory/controllers/logic module 378 includes pulse with modulation (PWM) logic 380, combinatorial logic 382, clock logic 384, pressure control logic 386, analog/digital converter logic 388, math unit logic 390, source sensor circuitry 392, band pass filter logic 394, response sensor circuitry 396, and long pass filter logic 398. Via the pressure control logic 386, the memory/controllers/logic module 378 is arranged to control any number and type of pressure control structures such as perifusate reservoir valves 400, pressure sources 402 (e.g., an air compressor, a compressed gas tank, a compressed gas cylinder, and the like), refrigeration sources 404 (e.g., ice chamber, refrigeration chamber, air conditioning chamber, or another cooling device), and optional microperifusion channel valves 405.

The pressure-driven, adjustable throughput fluidics (pressure-driven, adjustable throughput fluidics) system 300 presented in FIG. 6 has a control system 306 presented in more detail in FIG. 7. Embodiments of the pressure-driven, adjustable throughput fluidics system 300 may be arranged as a standalone or communicatively linked high throughput instrument configured to maintain and assess tissue in response to materials (e.g., drugs) and experimental conditions relevant to physiological and disease states.

The pressure-driven, adjustable throughput fluidics system 300 may be arranged for culturing and maintaining the function and viability of tissue or cells by providing a continuous flow of perifusate material (e.g., oxygenated media replete with substrate). The continuous flow performs the ongoing act of washing away waste products, such as lactate and ammonia, from the tissue or cells under test, which acts permit a test cycle to last for any desirable duration (e.g., minutes, hours, days). When properly controlled, the perifusate reservoir embodiments and microperifusion chamber embodiments described in the present disclosure are enabled to provide the continuous flow of perifusate material.

The pressure-driven, adjustable throughput fluidics system 300 is further arranged with a plurality of sensors arranged to independently or cooperatively assess key analytes produced or consumed by the tissue or cells of interest (i.e., the sample tissue or cells 132 (FIG. 1) under test). In some cases, the sensor logic (e.g., source sensor logic 362 and sense sensor logic 364) is optically-based. Sensor logic along these lines includes oxygen, oxidase-based sensors (e.g., for analysis of glucose, lactate, pyruvate, glutamate, xanthine, GABA, acetylcholine, aspartate, dopamine, epinephrine, norepinephrine), $CO_2$ sensors, CO sensors, ammonia sensors, nitric oxide sensors, and hydrogen sulfide sensors. Other optically-based sensors are also considered. In other cases, the sensor logic may be radio frequency (RF) based, audio frequency based (e.g., ultrasound), radiologically based (e.g., gamma-emitters, x-ray, magnetic resonance imaging (MRI)), or based on another physical property of cells, tissue, perifusate, or the like. The plurality of sensors (e.g., source control logic 362, sense control logic 364, source sensor circuitry 392, band pass filter 394, response sensor circuitry 396, and long pass filter circuitry 398) are suitably arranged to take direction from the control system 306 (e.g., via the PWM logic 380, combinatorial logic 382, clock logic 384, A/D converter logic 388, math unit logic 390).

And the pressure-driven, adjustable throughput fluidics system 300 is arranged with any number of valve structures to selectively adjust pressure in the system during any number of test cycles. Valves, for example, may be arranged in one or more locations in each pathway that perifusate flows, or causes perifusate to flow, in a microperifusion experiment. The valves may be located, for example, in one or more portions of the perifusate reservoir 302, one or more locations in the microperifusion channel 304, or in some other location. The valve structures are suitably arranged to take direction (e.g., control signals) from the control system 306 (e.g., via the pressure control logic 386), and the valve structures may also provide status information (e.g., amount a valve is open, amount a valve is closed, flow rate information, or the like) or other information back to the control system 306. Via the control system 306, experimental conditions may be automated to expose (e.g., bath) the tissue or cells under test to the desired perifusate material composition.

When the pressure-driven, adjustable throughput fluidics system 300 is suitably controlled as described herein, real time data is generated. The real time data reflects the tissue or cell responses of endpoint parameters to changes in experimental conditions. These end point parameters can be actual levels (e.g., of oxygen, lactates, or other parameters), or these endpoint parameters can be production/consumption rates as determined by the mathematical difference in inflow and outflow concentrations times the flow rate.

Table 1 lists several scenarios where data generated by pressure-driven, adjustable throughput fluidics system embodiments of the present disclosure may be used.

TABLE 1

Applications: Scenarios where technical data generated by pressure-driven, adjustable throughput fluidics system embodiments may be used Drug testing for both toxicity and efficacy. The decrement in $O_2$ consumption rate (OCR) in response to a drug, on its own or normalized by the rate of lactate production (LPR), is recognized as an objective function that flags risky compounds that have a high probability of off-target effects. Since changes in OCR also reflect changes in function, the parameter can be used to screed for efficacy of a particular material (e.g., drug).

Basic and applied research on cell physiology and disease states is notably aided by measurements of tissue function and viability. The pressure-driven, adjustable throughput fluidics system is designed to have wide utility with respect to a range of tissues important to a wide array of diseases, fine control of experimental conditions that include both aqueous and gas phase components of media, and measurement of endpoints that are relevant to many tissue functions.

Personalized medicine. The capability to rapidly assess a patient's own biopsied tissue makes it possible to test efficacy and toxicity of drugs that could generate an individualized regimen that is determined to be favorable for the specific patient. Examples are chemotherapeutic drugs tested on a patient's own tumor tissue, or as a diagnostic test of tissue sensitivity to insulin for diabetes research.

Environmental toxins. Compounds with unknown toxicity can be objectively quantified by using the system with standard reference tissue.

Quality control and lot testing for distribution of cells and tissue. Entities that distribute tissue for research purposes, as well as for transplantation, can be tested for release criteria and lot-to-lot variation Table 2 identifies several technical features that support achievable, actionable results produced by the pressure-driven, adjustable throughput fluidics system embodiments described in the present disclosure. Table 3 contrasts several of the technical features identified in Table 2 with corresponding limitations of conventional tissue and cell analysis systems.

TABLE 2

Differentiators: Technical features provided by pressure-driven, adjustable throughput fluidics system embodiments described in the present disclosure pressure-driven, adjustable throughput fluidics system embodiments are high-throughput fluidics systems that maintain and assesses a wide range of cell and tissue models. Tissue maintenance is facilitated by a constant flow of perifusate material containing physiologic (e.g., bicarbonate-based) media and continuous assessment generates readouts that are of high value. Conventional static incubation systems (e.g., as produced by SEAHORSE BIOSCIENCE, for example) and conventional multi-channel microfluidic cell culture systems (e.g., organ-on-a chip) either assess static 96-well plates or singularly analyze maintained cell cultures, but data is not useful if the tissue is not well maintained, as is the case in static systems, or if the cultures are not quantitatively evaluated, as with the organ-on-a-chip.
Well-maintained tissue as provided in the pressure-driven, adjustable throughput fluidics system embodiments described herein also allows for greater duration of experimental protocols needed for the evaluation of drugs and conditions that can take minutes, hours, days, or even weeks to proceed. The miniaturization of the pressure-driven, adjustable throughput fluidics system embodiments allows for greatly reduced need for a large volume of tissue or cells as sample test compounds, making it possible to do many tests from a single biopsy and other scarce tissue types.
Conventional fluidics systems are not scalable and are very complicated to use, greatly limiting their use.
The pressure-driven, adjustable throughput fluidics system embodiments meet the needs of the pharmaceutical industry and by concurrently operating a plurality (e.g., 32, 96, 128, 1024, etc.) of microperifusion channels. A large number of channels does not increase complexity of operating a modular, snap-together pressure-driven, adjustable throughput fluidics system
The use of flow and ultra-stable sensors in pressure-driven, adjustable throughput fluidics system embodiments enables substantial sensitivity over conventional methods. The sensitivity will reveal toxicity that is missed by in vitro assays currently in use as standards throughout the industry.
The use of flow and automated valves in pressure-driven, adjustable throughput fluidics system embodiments enables fine control of tissue exposure to drugs and conditions to include washout analysis as well as interaction between materials (e.g., drugs).
Integrating a plurality of sensors as a module enables assessment of multiple endpoints concurrently, which increases the power and interpretability of the generated data.

TABLE 3

Differentiators: Comparison and contrast of technical features between pressure-driven, adjustable throughput fluidics system embodiments and conventional technologies.

| Feature | pressure-driven, adjustable throughput fluidics System | Static Incubation | Organ-On-Chip |
| --- | --- | --- | --- |
| Tissue | Solid or Cells | Cells only | Solid or Cells |
| Continuous Assessment | Metabolism Function | Metabolism only | Neither |
| Sensitivity | Absolute Change = 0.3%/hour | Relative Change = 5%/hour | N/A |
| Protocol Duration | Minutes, Hours, Days, Weeks | 5 hours | 28 days |
| Throughput | Any number of channels | Up to 96 channels | 1 channel |
| $CO_2$ in Media Perifusate Control | Yes Washout, Multiple substance & concentrations, hypoxia | No Additions only | Yes Additions only |

Table 4 identifies several technical features and effects implemented in the pressure-driven, adjustable throughput fluidics system embodiments described herein, which effects are not available in the conventional tissue analysis technologies.

TABLE 4

Innovation: Technical features and effects implemented in
the pressure-driven, adjustable throughput fluidics system
embodiments and described in the present disclosure The replacement of peristaltic pumps found in conventional systems with gas
pressure-driven flow results in a perifusate drive system having an absence
of mechanical moving parts; the pressure-driven, adjustable throughput
fluidics system embodiments thus provide very fine control of perifusate flow
and can maintain a wide range of stable flow rates.
Some modules of the pressure-driven, adjustable throughput fluidics system
embodiments are 3D-printed, which allows for increased complexity with
respect to the number and tortuosity of microperifusion flow channels and
ports, and allows for a multi-channel fluidic system constructed within a single
piece of material.
In some pressure-driven, adjustable throughput fluidics embodiments,
configuration of independent pairs of excitation light sources and
photodetectors for each microperifusion channel with inexpensive and readily
available electrical components enabled the construction of a high-throughput
(e.g., 96-channels or more) optical detection system that is both sensitive and
stable.
Computer-controlled multi-channel valves in pressure-driven, adjustable
throughput fluidics system embodiments, where a single control element may
switch flow diversion of many perifusate conduits and in addition or the
alternative, many microperifusion channels.
Automated algorithms to process, report, and interpret large scale data sets
that are generated from the pressure-driven, adjustable throughput fluidics
system embodiments.

In at least some embodiments of a pressure-driven, adjustable throughput fluidics system 300, a scientific practitioner will create test cycles in which it is desirable to measure oxygen in the effluent perifusate material that has passed the sample tissue or cells under test. In at least one technique, oxygen is measured in the outflow of the selected microperifusion channel 104A based on an oxygen-sensitive dye affixed to a dye-carrying medium (e.g., a plastic strip, glass beads, or the like). The dye-carrying medium can be arranged (e.g., wedged) in the respective microperifusion channel 104A. The dye-carrying medium may, in some cases, be arranged about one tenth to about one half inch (≈0.10 in. to ≈0.50 in.) downstream from the sample tissue or cells.

In some cases, source sensor circuitry 392 includes a light emitting diode (LED). The LED may or may not emit light in the visible spectrum. The LED may be arranged, for example, to emit ultraviolet light in the 10 to 400 nanometers (nm) range (e.g., 315 nm, 390 nm). Alternatively the LED may be arranged to emit light in the 400 to 700 nm visible range (e.g., 620 nm (red), 460 nm (blue)) or some other wavelength range.

When the source sensor circuitry 392 is a light source, the source sensor circuitry 392, in operation, will be located "close" to the microperifusion channel 104A; particularly in proximity (e.g., adjacent) to the dye-carrying medium. In some cases, for example, the source sensor circuitry 392 may be located (e.g., mounted, placed, clamped, coupled, and the like) within about one half inch or closer (<≈0.5 in.). When the microperifusion channel 104A is fully or at least partially transparent or translucent, at least where the dye-carrying medium is located, light emitted by the source sensor circuitry 392 will impinge the oxygen-sensitive dye.

In some cases, where a microperifusion chamber is arranged as a module having a plurality of microperifusion channels, the source sensor circuitry 392 may include a corresponding module arranged for fixed or removable coupling to the microperifusion chamber module. In these cases, for each microperifusion channel in the microperifusion chamber module, the source sensor circuitry module will have at least one corresponding source sensor circuit.

In some cases, an optional bandpass filter 394 is arranged between the source sensor circuitry 392 and the microperifusion channel 104A. In cases where the bandpass filter 394 is included, the bandpass filter 394 is arranged to pass signals of a desired wavelength (e.g., about 390 nm) into the respective microperifusion channel 104A and block signals of other wavelengths from fully or partially entering the microperifusion channel 104A. In cases where the source sensor circuitry 392 includes a 390 nm LED, for example, the optional bandpass filter 394 will permit 390 nm signals to pass while blocking light signals of other wavelength from entering the microperifusion channel 104A. In this way, stray light, ambient light, and other light can be restricted from entering the microperifusion channel 104A.

In some embodiments, the optional bandpass filter 394 may be arranged as a rigid or flexible "strip" of bandpass filter material that is adhered or otherwise located (e.g., applied, stuck, and the like) on or about the microperifusion channel 104A.

In some cases, where the microperifusion chamber is arranged as a module having a plurality of microperifusion channels, for example, a series of optional bandpass filters 394 may be tuned to different wavelengths. Alternating optional bandpass filters 394 may be tuned to a first wavelength or a second wavelength, respectively. In this way, a corresponding module will have a plurality of source sensor circuits 392 with alternating wavelength light sources (i.e., alternating light sources that emit light of a first wavelength or a second wavelength). In operation, the plurality of source sensor circuits 392 may concurrently emit light, and since light from each alternating source has a different wavelength, the corresponding light will pass through its associated optional bandpass filter 394 while light from an adjacent source sensor circuit 392, which has a different wavelength, will be blocked.

Each source sensor circuit 392 implemented in a pressure-driven, adjustable throughput fluidics system 300 is associated with a response sensor circuit 396. In some cases, there is a one-to-one correspondence between source sensor circuits 392 and response sensor circuits 396. In other cases, there are more or fewer source sensor circuits 392 than there are response sensor circuits 396. In these non-one-to-one cases, one or the other of the source sensor circuits 392 and response sensor circuits 396 may be selectively moved during a test cycle, or one or the other of the source sensor circuits 392 and response sensor circuits 396 may be desirably located in a way that the respective circuit can service a plurality of microperifusion channels 104A.

Response sensor circuits 396 may include one or more photosensitive components. That is the response sensor circuits 396 may be formed from photodiodes, phototransistors, PIN diodes, or some other photoelectric circuit. Each response sensor circuit 396 is responsive to light entering an active (e.g., sensing) element of the circuit. In some cases, the response sensor circuits 396 outputs an analog signal corresponding to the light energy sensed by the circuit. In some cases, the output from the response sensor circuits 396 is a digital signal representative of the light energy received by the circuit. The output signal from the response sensor circuits 396 can represent an instantaneous light measurement, an accumulated light measurement, or some other indication of how much light has been "captured" by the circuit.

Along the lines of the optional bandpass filters 394, embodiments of the pressure-driven, adjustable throughput fluidics system 300 may include optional long pass filters 398. These types of filters are located between the dye-carrying medium and the corresponding response sensor circuit 396 (e.g., light detector) and serve to block emitted light from non-specific sources other than the dye (e.g., oxygen-sensitive dye). In at least one case, bandpass filter circuitry 394 is arranged to pass light having a wavelength of more than about 605 nm (>≈605 nm).

The optional band (e.g., long) pass filter 398 circuitry may be used to permit only light of a selected wavelength to enter the active sensor element of the respective response sensor circuit 396. Also along the lines of the optional bandpass filters 394, individual band (e.g., long) pass filters 398 may be arranged to pass alternating wavelengths or otherwise arranged such that adjacent filters are tuned to different wavelengths. In this way, a plurality of microperifusion channels in a modular microperifusion chamber can be operated concurrently, and test cycle operations of one channel will not affect operations of adjacent or otherwise nearby channels. In addition, the optional band (e.g., long) pass filters 398 may be formed and implemented individually, in a "strip," or in some other arrangement.

In some embodiments of the pressure-driven, adjustable throughput fluidics system 300, each source sensor circuit 392 is associated with a corresponding response sensor circuit 396. One of skill in the art will recognized that the sensor circuits may be light-based, radio frequency (RF) based, audio-based, or based on some other property of physics. Nevertheless, to simplify the present disclosure, the sensor circuits are described as being light sources and corresponding light detectors.

Turning again to FIG. 7, in at least one case, a source sensor circuit 392 LED is positioned on one side of a microperifusion channel 104A, and a corresponding response sensor circuit 396 is positioned on an opposite side of the microperifusion channel 104A for a test cycle. Both sensor circuits are positioned about the microperifusion channel 104A in a location at or near where an oxygen-sensitive dye material (e.g., a dye-carrying medium) will be located during the test cycle. A bandpass filter 394 is optionally positioned between the source sensor circuit 392 and the microperifusion channel 104A, and a long pass filter 398 is optionally positioned between the response sensor circuit 396 and the microperifusion channel 104A.

During the test cycle, the source sensor logic 362 directs the source sensor circuit 392 to emit light (e.g., 390 nm light). The control signal for the light emitted by the source sensor circuit 392 may be a pulse width modulation (PWM) signal generated by PWM logic 380, by a trim potentiometer, or by some other signal source. If the optional bandpass filter 394 is in place, the light entering the microperifusion channel 104A will come only or substantially from the source sensor circuit 392. Correspondingly, if the optional long pass filter 398 is in place, light from sources other than the source sensor circuit 392 or the oxygen-sensitive dye material is blocked from entering the response sensor circuit 396, and light from the source sensor circuit 392 and light excited by the oxygen-sensitive dye material will be passed to the response sensor circuit 396. Accordingly, during the test cycle, light from the source sensor circuit 392, and the emitted light from the oxygen-sensitive dye material, both traverse the "walls" of the 3D-printed microperifusion chamber (about 3 mm thick).

The inventors have recognized that the transmittance of light through the microperifusion chamber is less than that of glass (e.g., only about 20% of transmittance through glass). Nevertheless, the reduction of light signal strength is partially offset by positioning the source sensor circuitry 392 and response sensor circuitry 396 up against the microperifusion chamber adjacent to the microperifusion channel of interest. In addition, the inventors have recognized that the received light signal is an accurate representation of the light produced by the oxygen-sensitive dye even if the signal is attenuated. Accordingly, an inexpensive and reliable pressure-driven, adjustable throughput fluidics system 300 that employs light sources and light sensors to independently monitor oxygen-sensitive dye can be constructed with readily available materials, and the system can be modularized and scaled to any desirable number of channels (e.g., 8 channels, 32 channels, 96 channels, or any other number of channels)

During a test cycle, a signal from the dye, as instigated by a source signal from the source sensor circuit 392, travels to the response sensor circuit 396. In some cases, the response sensor circuit 396 is formed as a photodiode detector operated with zero volts of direct current (0 VDC) bias. In cases where the response sensor circuit 396 generates an analog electrical signal, the signal may be buffered or otherwise conditioned by various circuitries (e.g., a current-to-voltage amplifier followed by a second amplifier, which provides gain and anti-aliasing) as indicated by the dashed line around the response sensor circuit 396 and long pass filter 398. The conditioned signal from the response sensor circuit 396 is passed to analog/digital (A/D) converter logic 388, which produces a digital representation of the signal received at the response sensor circuit 396. As directed by the sense sensor logic 364, any number of samples may be collected over time (e.g., according to clock logic 384). Math unit logic 390 may be used to average collected samples, In some embodiments, collected, averaged, and otherwise processed sample data is communicated to the remote computing server 306B via one or both of the wired and wireless communication interfaces 372A, 372B. In at least one case, the data is ported via an asynchronous serial connection to a serial-to-USB cable plugged into a standard communications port of a personal computer (PC).

In some embodiments, the timing and synchronization of the source sensor circuit 392 activation and the response sensor circuit 396 acquisition is controlled according to the clock logic 384, which may include a precision crystal oscillator frequency reference used to set one or more system clocks of the control logic 306. Current in the source sensor circuit 392 (e.g., current in an LED) may be controlled by signal conditioning circuits represented by the dashed lines around the source sensor circuit 392 and band pass filter 394. The signal conditioning circuits may include, for example, bipolar transistor current sources, an operational amplifier-based feedback loop, and other such circuits.

Figure 8:
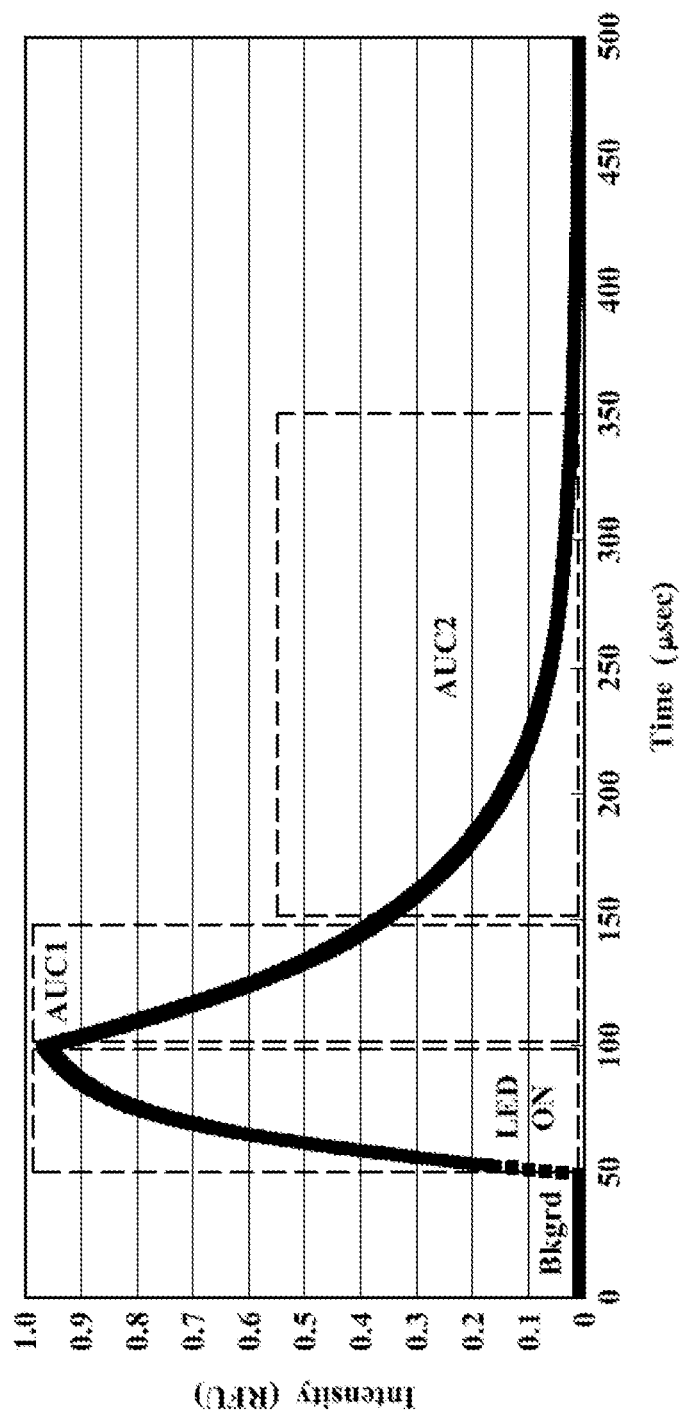
FIG. 8 is a timing diagram showing exemplary signal generation and processing.

FIG. 8 is a timing diagram showing exemplary signal generation and processing. The signals represented in FIG. 8 are generated and processed by embodiments of a pressure-driven, adjustable throughput fluidics system 300. Reference is made to the embodiments of FIGS. 6 and 7. The acquisition of raw data in some embodiments of the pressure-driven, adjustable throughput fluidics system 300 is directed by the sense sensor logic 364, which cooperates with the source sensor logic 392. Timing may be controlled or otherwise determined according to clock logic 384.

In some cases, the data collected during signal generation and processing of FIG. 8 may represent or otherwise be considered as a measurement of the phosphorescent decay rate of an oxygen-sensitive dye. And the phosphorescent decay rate may be indicative of the oxygen consumption rate (OCR) of the specific tissue or cell sample under test. Stated differently, the OCR is the rate at which the tissue sample absorbs oxygen from the perifusate material flowing through the tissue in the microperifusion channel 104A. Hence, the OCR is an integrated measure of energy generation that reflects changes in cell number, viability, and energy utilizing cellular processes. OCR may, for example, be measured as the decrement in oxygen concentration (i.e., partial pressure of oxygen, pO2, or pO2) times the flow rate of perifusate material flowing through the tissue sample.

In a first, left-most portion of the timing diagram of FIG. 8, a background period of time is permitted to pass. The background time in FIG. 8 is about 50 microseconds (≈50 μS), but any suitable other time may also be selected. For each of many data collection events during a test cycle, prior to the emission of a source signal, background intensity of an input signal at the response sensor circuitry 396 is determined. This background intensity can be measured as the average intensity of a determined number of points over a determined time period. In FIG. 8, the background intensity is measured as 48 data points collected over about 48 μS during the background time.

After passage of the background time, a source signal is emitted. In FIG. 8, the source signal emission is indicated as "LED on." The timing of the source signal (e.g., an LED pulse from source sensor circuitry 392) and the sampling of data (e.g., by light samples collected with response sensor circuitry 396) centers around the source emission (e.g., the pulse of LED light) of a determined duration. In some cases, as represented in FIG. 8, the source signal emission may be about 50 microseconds (≈50 μS). Other time durations of the source signal are contemplated.

Following the emission of the source signal, detected signals are collected (e.g., by the response sensor circuitry 396 under direction of the sense sensor logic 364) at a determined sampling rate. The determine sampling rate may be one megahertz (1 MHz) for example, as represented in FIG. 8, but other sampling rates are contemplated. The detected signals may be captured in real time, periodically, until the decay of the signal is near completion. Decay of the signal may be about 250 microseconds (≈250 μS) as indicated in FIG. 8, but other decay timing is contemplated.

After termination of the source signal, data collection may be delayed to ensure with acceptable confidence that the source sensor circuitry 392 is actually "off." In FIG. 8, this delay period about two to four microseconds (≈2 μS-≈4 μS), but other delay periods are contemplated.

Collection of oxygen-based data occurs after the delay period in one or more windows. Two windows are represented in FIG. 8, but other numbers of windows are also contemplated. In exemplary embodiments described herein, area-under-curve (AUC) measurements are collected and determined in two regions. The AUC is calculated by summing the products of the measured intensity for each time point, subtracting the background measurement data, and the delta time (i.e., 1 μS in the embodiment of FIG. 8) for all times within each time window. The ratio of the AUCs, the endpoint that is related to the $O_2$ tension, is calculated according to Equation 2.

$$\text{Ratio} = \sum_{j=1}(Intj - Bkg) \Big/ \sum_{i=1}(Inti - Bkg) \qquad \text{q.2}$$

where
i=the points in window 1 and
j=the points in window 2.

The exemplary data in FIG. 8 is shown for Window 1 demarcated by about 4 μS to 34 μS following the cessation of an LED pulse, and about 34 μS to 250 μS for Window 2. In some embodiments of test cycles, very accurate and useful data is produced from a large numbers of decay curves being averaged (e.g., 10,000 curves per time point). In some cases, the decay curves are averaged by the math unit logic 390. In other cases, raw data is communicated to the remote computing device 306B for averaging, calculation of areas under the curve, real time graphing, and further processing.

The data acquisition and processing of a pressure-driven, adjustable throughput fluidics system 300 may be controlled by a scientific practitioner in many ways. In some cases, for example, a scientific practitioner will enter processing parameters for the pressure-driven, adjustable throughput fluidics system 300. In at least some embodiments, the practitioner can define time intervals over which signal-to-noise ratios and curve slopes may be calculated. In some embodiments, the practitioner can define background timing, source signal timing, window size timing, source signal intensity, source signal wavelength, and any number of other parameters. In still other embodiments, the types of parameter definitions available to a scientific practitioner are considered in two ways. A first type of parameter definition includes technical parameters. A second type of parameter definition includes test-cycle specific parameters.

Technical parameters controllable by a scientific practitioner in at least some embodiments of a pressure-driven, adjustable throughput fluidics system 300 include, without limitation, number of decay curves averaged per time point, LED power, LED start, LED stop, dark count time, area 1 start, area 2 start, area 2 stop, and gain (response sensor circuitry 396). Test-cycle specific parameters controllable by a scientific practitioner in at least some embodiments of a pressure-driven, adjustable throughput fluidics system 300 include, without limitation, output file name, time interval for data collection (in minutes), time window of collection (in hours) (program can be halted or paused by entry of a specific keyboard key), comments at specific times, and experimental conditions for each channel.

Returning to FIG. 7, it is recognized that the control system 306 may be formed in many different ways without departing from the spirit of the present inventive concepts. Along these lines, the logic represented in the control system 306 of FIG. 7, and particularly the logic of the electronic logic module 306A may be implemented by hardware, software, or a combination of hardware and software. The various logic modules, for example, may be comprised partially or completely in software executed by the processor 360. Alternatively, or in addition, the various logic modules may be comprised as state machines, independent logic device, circuitry, or any suitable combination thereof.

Having collected data, and in some cases pre-processed the data, the data may be ported from the electronic logic module 306A to the remote computing server 306B via one of the available wired or wireless communications interfaces 372A, 372B. The data may be communicated in real time, and the data can be plotted in any number of scientific practitioner controlled formats. In addition, calculations may be made in real time, so that quality control issues can be raised early and scientifically useful results can be highlighted, thereby facilitating decision-making during the test cycle of any given experiment.

Figure 9:
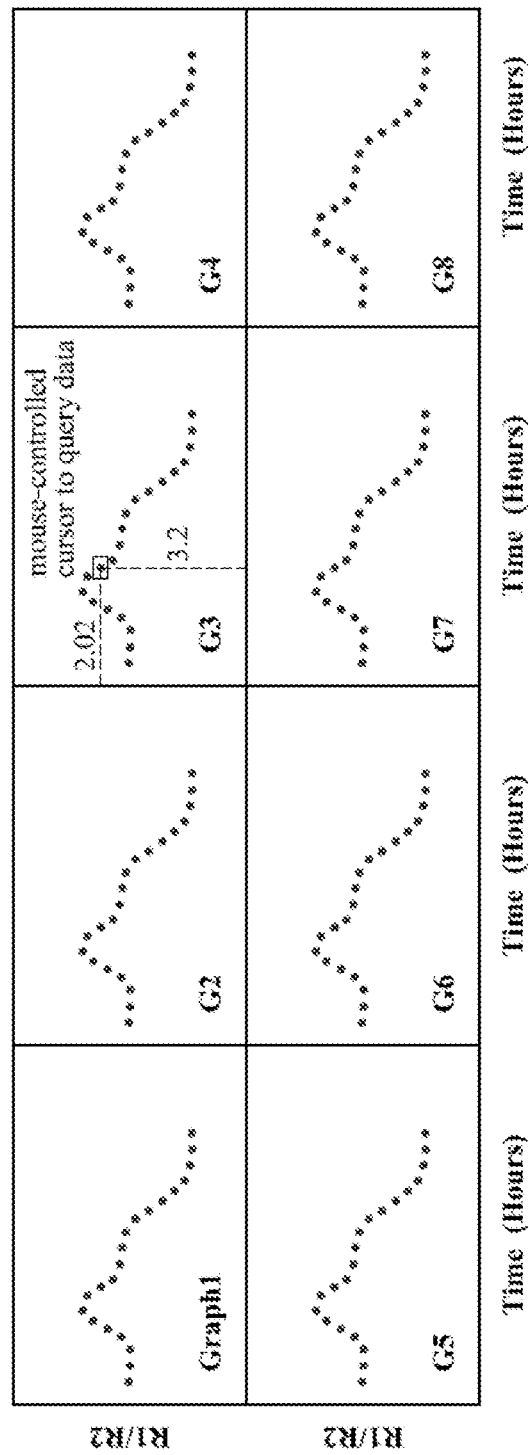
FIG. 9 is a plurality of exemplary data graphs produced with data collected by the pressure-driven, adjustable throughput fluidics system embodiments.

FIG. 9 is a plurality of exemplary data graphs produced with data collected by pressure-driven, adjustable throughput fluidics system embodiments. In FIG. 9, ratio data as generated in accordance with Equation 2 can be graphed in real time in multiple ways. Eight distinct graphs are shown in FIG. 9, for example, and each of the graphs can be shown individually or collectively on a display screen or other presentation device. The microperifusion channels to be graphed can be controlled by the scientific practitioner. Data can be scrolled through any number of microperifusion channels (e.g., 1-96), or alternatively, the scientific practitioner can display the microperifusion channel data as individual or groups of plots.

In some cases, for instance, select microperifusion channel data of a test substance can be plotted against the control substance, or as groups in a dose response. Since slope and signal-to-noise (S/N) are calculated in real time, graphs can be plotted of all microperifusion channels whose slope is significantly different from the control. In a typical experiment's test cycle, drugs or changes in conditions are assessed after a steady state is reached. To track this during the initial stages of an experiment, microperifusion channels whose baseline is still changing, or microperifusion channels where the S/N remains unacceptable, can be displayed. In this way, the scientific practitioner can assess when it is suitable to start the experimental test cycle perturbations, and the scientific practitioner can initiate one or more phases of the test cycle. The scientific practitioner can also view plots of temperature, humidity, mass, and any other data, and the scientific practitioner can adjust technical and test cycle specific parameters to make appropriate corrections.

In consideration of the output data, the scientific practitioner may also control several outputs of data produced by exemplary pressure-driven, adjustable throughput fluidics systems 300. The scientific practitioner may, for example, control indexes, time stamp, time stamped comments, temperature, microperifusion channel areas-under-curve data and calculations output, microperifusion channel ratios, microperifusion channel ratio data display (e.g., (100*stdev (Ratio)/mean (Ratio)) over a scientific practitioner selected time window, microperifusion channel S/N indicator (e.g., to flags to the scientific practitioner that (100*sd/mean) is above a specified value), microperifusion channel slope (i.e., ratio) (e.g., over a scientific practitioner selected time window in minutes, which is typical before and/or after adding a material of interest such as a drug), microperifusion channel slope indicator (e.g., which flags the scientific practitioner that slope is above a specified value (i.e., that the slope is not flat and the experiment should not yet proceed), and other such output data.

In some of these cases, Ratio_StDev is calculated over a specified time intervals where there are no changes in experimental conditions, so the signal should be unchanging. In some of these cases, Ratio_slope is calculated before a change in experimental condition, such as the addition of a drug, to establish that the baseline is flat. This value can then be used over appropriate time intervals to establish the effect of a drug relative to control, and when drug effects have plateaued.

In some tests discussed herein, from the output from the response sensor circuitry 396 (e.g., outflow oxygen sensor data), the oxygen consumption rate (OCR) is calculated by the difference between the inflow and outflow of oxygen times the perifusate flow rate. The perifusate flow rate can be estimated from a nomagraph constructed by previously obtained data after validating that perifusate flow in each microperifusion channel was accurately related to the length and inside diameter of the conduits (e.g., resistance tubes) and the gas-pressure set by the regulation means. Inflow oxygen can be determined in a number of ways, including, for example, by calibration of the oxygen signal relating lifetime to oxygen, or by changing the perifusate flow rate at regular intervals during a test cycle. By determining the inflow oxygen level at the start of the experiment, OCR can be calculated and plotted in real time.

Figure 10:
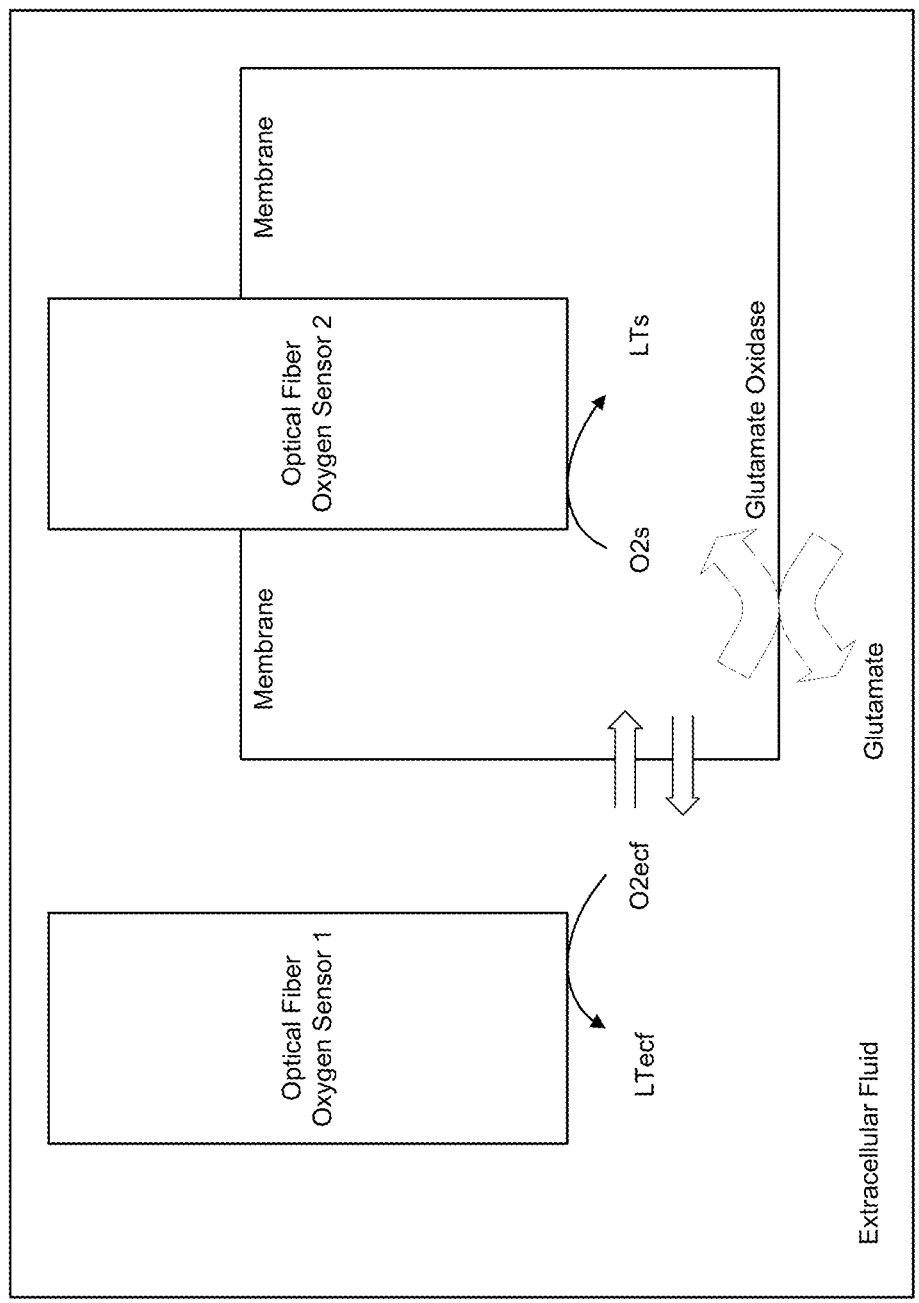
FIG. 10 is an oxygen sensor and an oxygen sensor embedded oxidase configuration to enable measurement of glutamate or other compounds where the appropriate oxidase is available.

FIG. 10 is an oxygen sensor and an oxygen sensor embedded oxidase configuration to enable measurement of glutamate or other compounds where the appropriate oxidase is available. In some embodiments, the perifusate material outflow port 352 (FIG. 6) in an exemplary pressure-driven, adjustable throughput fluidics system 300 is modified with the illustrated optical fiber oxygen sensors and membranes. In this case, sensors of various analytes are situated in the perifusate outflow of each microperifusion channel, downstream of the sample tissue or cells under test. To detect oxygen, a platinum porphyrin is used that is affixed to a glass rod by dissolving the dye in a polymer such as polycarbonate, and baking it on to the glass. By embedding an oxidase into the O2-sensitive dye, analytes where the associated oxidase is available can be measured as shown in FIG. 10.

Figure 11:
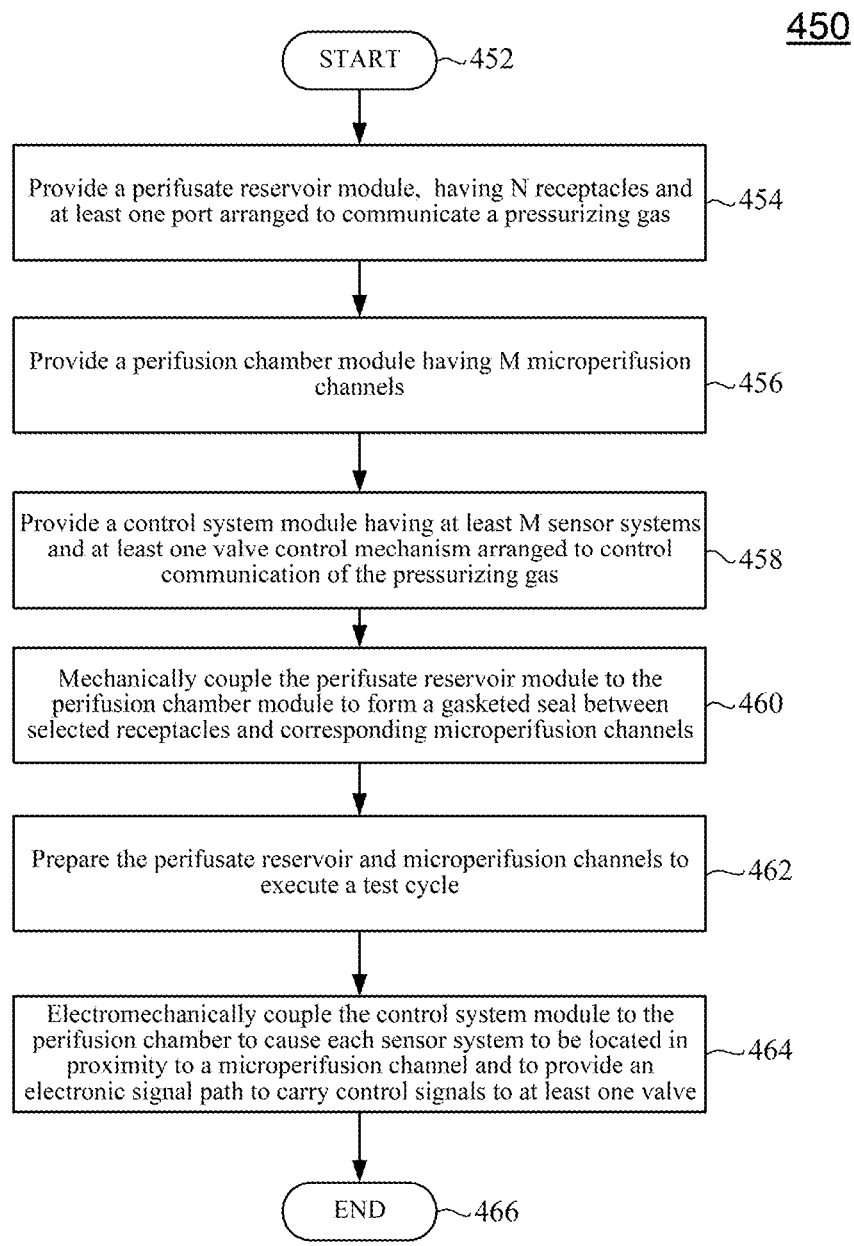
FIG. 11 is a data flow diagram representing a first pressure-driven, adjustable throughput fluidics system procedure.

FIG. 11 a data flow diagram representing a first pressure-driven, adjustable throughput fluidics (pressure-driven, adjustable throughput fluidics) system procedure 450.

At 452, processing begins in the first pressure-driven, adjustable throughput fluidics system procedure 450. The procedure 400 is directed toward a method of performing microperifusion.

At 454, a perifusate reservoir module is provided. The perifusate reservoir module has N receptacles, and the perifusate reservoir module has at least one port arranged to communicate a pressurizing gas into or out from the perifusate reservoir module. In some cases, the perifusate reservoir module is along the lines of perifusate reservoirs 102, 202, 302 described in the present disclosure.

At 456, a perifusion chamber module is provided. The perifusion chamber module has M microperifusion channels. Some embodiments of the perifusion chamber module of 406 are along the lines of perifusion chambers 104, 204, 304 described in the present disclosure.

At 458, a control system module is provided, The control system module has at least M sensor systems and at least one valve control mechanism. The at least one valve control mechanism is arranged to control communication of the pressurizing gas. The control system module is along the lines of the control system module 306 in the present disclosure.

At 460, a liquid perifusate material is added to each of the N receptacles, and at 462, the perifusate reservoir module I s mechanically coupled to the perifusion chamber module. The mechanical coupling forms a gasketed seal between selected ones of the N receptacles and corresponding ones of the M microperifusion channels.

At 464, the control system module is electromechanically coupled to the perifusion chamber. The coupling causes each of the M sensor systems to be located in proximity to a respective one of the M microperifusion channels, and this electromechanical coupling is arranged to provide an electronic signal path to carry control signals to at least one valve.

Processing of procedure 450 ends at 466. In many cases, however, processing does not end for several minutes, hours, days, or some other even longer duration. A test cycle procedure carried out in accordance with FIG. 11 can last any duration desired by a scientific practitioner.

Figure 12:
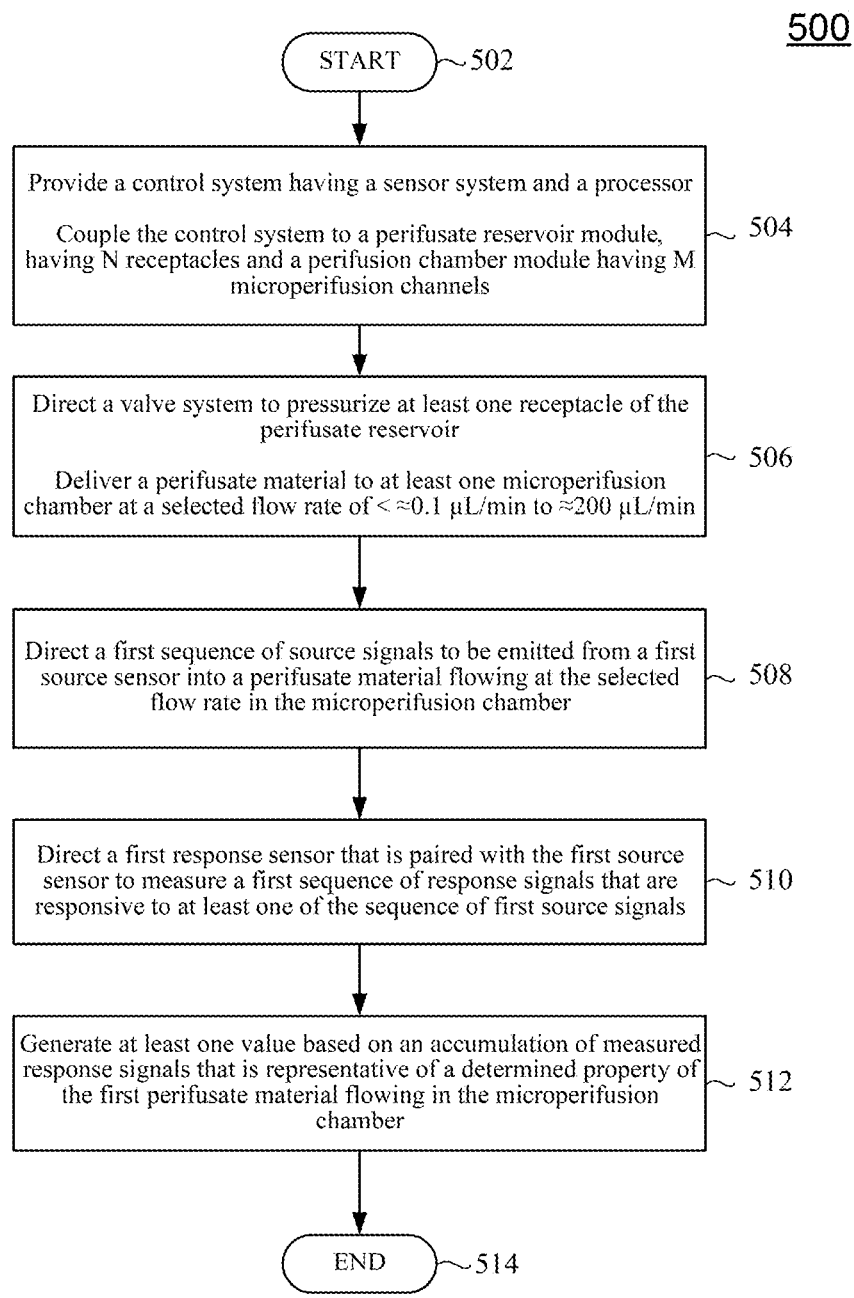
FIG. 12 is a data flow diagram representing a second pressure-driven, adjustable throughput fluidics system procedure.

FIG. 12 is a data flow diagram representing a second pressure-driven, adjustable throughput fluidics (pressure-driven, adjustable throughput fluidics) system procedure 500.

At 502, the procedure begins. The procedure 500 is directed toward operations of a control system for a microperifusion system such as the pressure-driven, adjustable throughput fluidics system 300 of FIG. 6, which has a control system 306.

At 504, the control system is provided. The control system has a processor and a sensor system. The sensor system includes a plurality of source sensors and a plurality of response sensors. Each of the source sensors is pairable with a corresponding response sensor, and each of the source sensor/response sensor pairs is arranged to communicate through a microperifusion channel. The control system is coupled to a perifusate reservoir module, which has N receptacles, and the control system is coupled to a perifusion chamber module, which has M microperifusion channels. The perifusate reservoir module is also coupled to the microperifusion chamber in sealed fluid communication. The processor is arranged to execute a test cycle having a determined duration.

At 506, the control system directs a valve system to pressurize at least one receptacle of the perifusate reservoir. The pressurization causes delivery of a perifusate material to at least one microperifusion chamber at a selected flow rate of less than about one-tenth microliter per minute to about 200 microliters per minute (<≈0.1 µL/min to ≈200 µL/min).

At 508, the control system directs a first sequence of source signals to be emitted from a first source sensor into a perifusate material flowing at the selected flow rate in the microperifusion chamber.

At 510, the control system directs a first response sensor that is paired with the first source sensor to measure a first sequence of response signals. Each one of the first sequence of response signals is responsive to at least one of the sequence of first source signals.

At 512, at least one value based on an accumulation of measured response signals is generated. The at least one value represents a determined property of the first perifusate material flowing at the selected flow rate in the respective one of the microperifusion chambers.

Processing of procedure 500 ends at 514. In many cases, however, processing does not end for several minutes, hours, days, or some other even longer duration. A test cycle procedure carried out in accordance with FIG. 1 can last any duration desired by a scientific practitioner.

In operation, embodiments of the pressure-driven, adjustable throughput fluidics system 300 (FIG. 6) are initially deployed with perifusion media bearing physiological and pharmaceutical test substances. pressure-driven, adjustable throughput fluidics systems 300 deployed in this way facilitate high-throughput physiological research and industrial toxicity screening. Hence these pressure-driven, adjustable throughput fluidics systems 300 have the advantage of providing continuous and quantitative measures of a variety of physiological tissue and cellular responses during experimental protocols that can last for seconds, minutes, hours, or even many days. Other perifusion media elements are contemplated, and many different types of perifusate materials (e.g., liquids, gasses, suspensions, and the like) are contemplated.

In commercial use of embodiments of the pressure-driven, adjustable throughput fluidics systems 300 described herein, oxygen consumption rate (OCR) data can be utilized in many ways depending on the scientific questions being addressed. It is known that standard protocols for testing drug effects will be to measure the decrement in OCR from the baseline as a function of time. Groups of compounds tested are ranked according to the OCR decrement. Once a statistically significant number of compounds are tested, then benchmarks for the decrements can be defined with respect to safety of the compounds in animal and human safety tests. Benchmarks will be defined based on the percent change from baseline at various multiples of therapeutic concentrations.

Having now set forth certain embodiments, further clarification of certain terms used herein may be helpful to providing a more complete understanding of that which is considered inventive in the present disclosure.

In the embodiments of present disclosure, one or more particular fluids are arranged to flow in a perifusion system such as the pressure-driven, adjustable throughput fluidics (pressure-driven, adjustable throughput fluidics) system 300 of FIG. 6. The various components and devices of the embodiments are interchangeably described herein as "coupled," "connected," "attached," and the like. It is recognized that once assembled, the system is suitably sealed to prevent fluid from escaping the system. The materials and the junctions formed at the point where two or more structures meet in the present embodiments are sealed to a mechanically, medically, or otherwise industrially acceptable level.

Furthermore, in the present disclosure, the passages that enable fluid to flow may be described as lumens, conduits, or the like. These passages, which may be thought of as a cavity in or through a tubular structure, may also be interchangeably identified herein as a port, tube, or other similar void as the circumstances may provide. The passages may have a circular cross-section, ovular cross-section, square cross-section, or a cross-section of any one or more suitable shapes. The passages may be formed from a single material or combination of materials at the time of construction (e.g., during a three-dimensional (3D) printing process). Alternatively, the passages may be formed as a distinct act in the process of construction (e.g., boring, drilling, tunneling, piercing, perforating, or the like).

FIG. 11 includes a data flow diagram illustrating a non-limiting process that may be used by embodiments of a pressure-driven, adjustable throughput fluidics (pressure-driven, adjustable throughput fluidics) system 300. In this regard, each described process may represent a module, segment, or portion of software code, which comprises one or more executable instructions for implementing the specified logical function(s). It should also be noted that in some implementations, the functions noted in the process may occur in a different order, may include additional functions, may occur concurrently, and/or may be omitted.

The figures in the present disclosure illustrate portions of one or more non-limiting computing device embodiments such as one or more components of control system 106. The computing devices may include operative hardware found in conventional computing device apparatuses such as one or more processors, volatile and non-volatile memory, serial and parallel input/output (I/O) circuitry compliant with various standards and protocols, wired and/or wireless networking circuitry (e.g., a communications transceiver), one or more user interface (UI) modules, logic, and other electronic circuitry.

Processing devices, or "processors," as described herein, include central processing units (CPU's), microcontrollers (MCU), digital signal processors (DSP), application specific integrated circuits (ASIC), peripheral interface controllers (PIC), state machines, and the like. Accordingly, a processor as described herein includes any device, system, or part thereof that controls at least one operation, and such a device may be implemented in hardware, firmware, or software, or some combination of at least two of the same. The functionality associated with any particular processor may be centralized or distributed, whether locally or remotely. Processors may interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, one or more embodiments describe software executable by the processor, which when executed, carries out one or more of the method acts.

As known by one skilled in the art, a computing device has one or more memories, and each memory comprises any combination of volatile and non-volatile computer-readable media for reading and writing. Volatile computer-readable media includes, for example, random access memory (RAM). Non-volatile computer-readable media includes, for example, read only memory (ROM), magnetic media such as a hard-disk, an optical disk, a flash memory device, a CD-ROM, and/or the like. In some cases, a particular memory is separated virtually or physically into separate areas, such as a first memory, a second memory, a third memory, etc. In these cases, it is understood that the different divisions of memory may be in different devices or embodied in a single memory. The memory in some cases is a non-transitory computer medium configured to store software instructions arranged to be executed by a processor. Some or all of the stored contents of a memory may include software instructions executable by a processing device to carry out one or more particular acts.

The computing devices illustrated herein may further include operative software found in a conventional computing device such as an operating system or task loop, software drivers to direct operations through I/O circuitry, networking circuitry, and other peripheral component circuitry. In addition, the computing devices may include operative application software such as network software for communicating with other computing devices, database software for building and maintaining databases, and task management software where appropriate for distributing the communication and/or operational workload amongst various processors. In some cases, the computing device is a single hardware machine having at least some of the hardware and software listed herein, and in other cases, the computing device is a networked collection of hardware and software machines working together in a server farm to execute the functions of one or more embodiments described herein. Some aspects of the conventional hardware and software of the computing device are not shown in the figures for simplicity.

When so arranged as described herein, each computing device may be transformed from a generic and unspecific computing device to a combination device arranged comprising hardware and software configured for a specific and particular purpose such as to provide a determined technical solution. When so arranged as described herein, to the extent that any of the inventive concepts described herein are found by a body of competent adjudication to be subsumed in an abstract idea, the ordered combination of elements and limitations are expressly presented to provide a requisite inventive concept by transforming the abstract idea into a tangible and concrete practical application of that abstract idea.

The embodiments described herein use computerized technology to improve the technology of perifusion, but there other techniques and tools remain available to assess cell and tissue function. Therefore, the claimed subject matter does not foreclose the whole or even substantial perifusion technological area. The innovation described herein uses both new and known building blocks combined in new and useful ways along with other structures and limitations to create something more than has heretofore been conventionally known. The embodiments improve on computing systems which, when un-programmed or differently programmed, cannot perform or provide the specific pressure-driven, adjustable throughput fluidics (pressure-driven, adjustable throughput fluidics) system features claimed herein. The embodiments described in the present disclosure improve upon known perifusion processes and techniques. The computerized acts described in the embodiments herein are not purely conventional and are not well understood. Instead, the acts are new to the industry. Furthermore, the combination of acts as described in conjunction with the present embodiments provides new information, motivation, and business results that are not already present when the acts are considered separately. There is no prevailing, accepted definition for what constitutes an abstract idea. To the extent the concepts discussed in the present disclosure may be considered abstract, the claims present significantly more tangible, practical, and concrete applications of said allegedly abstract concepts. And said claims also improve previously known computer-based systems that perform perifusion operations.

Software may include a fully executable software program, a simple configuration data file, a link to additional directions, or any combination of known software types. When a computing device updates software, the update may be small or large. For example, in some cases, a computing device downloads a small configuration data file to as part of software, and in other cases, a computing device completely replaces most or all of the present software on itself or another computing device with a fresh version. In some cases, software, data, or software and data is encrypted, encoded, and/or otherwise compressed for reasons that include security, privacy, data transfer speed, data cost, or the like.

Database structures, if any are present in the perifusion systems described herein, may be formed in a single database or multiple databases. In some cases hardware or software storage repositories are shared amongst various functions of the particular system or systems to which they are associated. A database may be formed as part of a local system or local area network. Alternatively, or in addition, a database may be formed remotely, such as within a distributed "cloud" computing system, which would be accessible via a wide area network or some other network.

Input/output (I/O) circuitry and user interface (UI) modules include serial ports, parallel ports, universal serial bus (USB) ports, IEEE 802.11 transceivers and other transceivers compliant with protocols administered by one or more standard-setting bodies, displays, projectors, printers, keyboards, computer mice, microphones, micro-electro-mechanical (MEMS) devices such as accelerometers, and the like.

In at least one embodiment, devices such as the control system 106 may communicate with other devices via communication over a network. The network may involve an Internet connection or some other type of local area network (LAN) or wide area network (WAN). Non-limiting examples of structures that enable or form parts of a network include, but are not limited to, an Ethernet, twisted pair Ethernet, digital subscriber loop (DSL) devices, wireless LAN, Wi-Fi, Worldwide Interoperability for Microwave Access (WiMax), or the like.

In the present disclosure, memory may be used in one configuration or another. The memory may be configured to store data. In the alternative or in addition, the memory may be a non-transitory computer readable medium (CRM). The CRM is configured to store computing instructions executable by a processor of the control system 106. The computing instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of a pressure-driven, adjustable throughput fluidics (pressure-driven, adjustable throughput fluidics) system.

Buttons, keypads, computer mice, memory cards, serial ports, bio-sensor readers, touch screens, and the like may individually or in cooperation be useful to a scientific practitioner operating the pressure-driven, adjustable throughput fluidics (pressure-driven, adjustable throughput fluidics) system. The devices may, for example, input control information into the system. Displays, printers, memory cards, LED indicators, temperature sensors, audio devices (e.g., speakers, piezo device, etc.), vibrators, and the like are all useful to present output information to the scientific practitioner operating the pressure-driven, adjustable throughput fluidics (pressure-driven, adjustable throughput fluidics) system. In some cases, the input and output devices are directly coupled to the control system 106 and electronically coupled to a processor or other operative circuitry. In other cases, the input and output devices pass information via one or more communication ports (e.g., RS-232, RS-485, infrared, USB, etc.).

As described herein, for simplicity, a scientific practitioner may in some cases be described in the context of the male gender. It is understood that a scientific practitioner can be of any gender, and the terms "he," "his," and the like as used herein are to be interpreted broadly inclusive of all known gender definitions. As the context may require in this disclosure, except as the context may dictate otherwise, the singular shall mean the plural and vice versa; all pronouns shall mean and include the person, entity, firm or corporation to which they relate; and the masculine shall mean the feminine and vice versa.

The terms, "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis (e.g., interrogating a photoelectric device to determine an oxygen consumption rate (OCR) during transmission of a perifusate in a given test cycle). An example of an activity that is not real-time is one that occurs over an extended period of time (e.g., hours or days) or that occurs based on intervention or direction by a scientific practitioner or other activity.

In the absence of any specific clarification related to its express use in a particular context, where the terms "substantial" or "about" in any grammatical form are used as modifiers in the present disclosure and any appended claims (e.g., to modify a structure, a dimension, a measurement, or some other characteristic), it is understood that the characteristic may vary by up to 30 percent. For example, a perifusion channel may be described as being formed or otherwise oriented "substantially vertical," In these cases, a channel that is oriented exactly vertical is oriented along a "Z" axis that is normal (i.e., 90 degrees or at right angle) to a plane formed by an "X" axis and a "Y" axis. Different from the exact precision of the term, "vertical," the use of "substantially" to modify the characteristic permits a variance of the "vertical" characteristic by up to 30 percent. Accordingly, a perifusion channel that is oriented "substantially vertical" includes perifusion channels oriented between 63 degrees and 117 degrees. A perifusion channel that is oriented at 45 degrees of an X-Y plane, however, is not mounted "substantially vertical." As another example, a perifusion channel having a particular linear dimension of "between about three (3) inches and five (5) inches" includes such devices in which the linear dimension varies by up to 30 percent, Accordingly, the particular linear dimension of the perifusion channel may be between one point five (1.5) inches and six point five (6.5) inches.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, the technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein.

The terms "include" and "comprise" as well as derivatives and variations thereof, in all of their syntactic contexts, are to be construed without limitation in an open, inclusive sense, (e.g., "including, but not limited to"). The term "or," is inclusive, meaning and/or. The phrases "associated with" and "associated therewith," as well as derivatives thereof, can be understood as meaning to include, be included within, interconnect with, contain, be contained within, connect to or with, couple to or with, be communicable with, cooperate with, interleave, juxtapose, be proximate to, be bound to or with, have, have a property of, or the like.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content and context clearly dictates otherwise. It should also be noted that the conjunctive terms, "and" and "or" are generally employed in the broadest sense to include "and/or" unless the content and context clearly dictates inclusivity or exclusivity as the case may be. In addition, the composition of "and" and "or" when recited herein as "and/or" is intended to encompass an embodiment that includes all of the associated items or ideas and one or more other alternative embodiments that include fewer than all of the associated items or ideas.

In the present disclosure, conjunctive lists make use of a comma, which may be known as an Oxford comma, a Harvard comma, a serial comma, or another like term. Such lists are intended to connect words, clauses or sentences such that the thing following the comma is also included in the list.

The headings and Abstract of the Disclosure provided herein are for convenience only and do not interpret the scope or meaning of the embodiments.

The pressure-driven, adjustable throughput fluidics (pressure-driven, adjustable throughput fluidics) systems described in the present disclosure provide several technical effects and advances to the field of cellular and tissue study. The pressure-driven, adjustable throughput fluidics systems achieve very low perifusate flow rates (e.g., <0.1-200 µL/min), which are driven in a pulse-less manner by the pressure of the physiologic gas (e.g., 5% $CO_2$, balance air) that overlies and equilibrates with perifusate material in the perifusate receptacles of the perifusate reservoir. In addition, the perifusate material that flows in a plurality of microperifusion channels can be contemporaneously (e.g., simultaneously) switched in real time from a control perifusate to a test perifusate in any number of microperifusion channels simply by pressurizing or changing the pressure in one or more perifusate receptacles (e.g., the first perifusate receptacle storing a test compound).

The various embodiments described above can be combined to provide further embodiments. Various features of the embodiments are optional, and, features of one embodiment may be suitably combined with other embodiments. Aspects of the embodiments can be modified, if necessary to employ concepts of the various patents, application and publications to provide yet further embodiments.

Example A-1 is a microperifusion method, comprising: providing a perifusate reservoir module, the perifusate reservoir module having N receptacles, and the perifusate reservoir module having at least one port arranged to communicate a pressurizing gas into or out from the perifusate reservoir module; providing a perifusion chamber module, the perifusion chamber module having M microperifusion channels; providing a control system module, the control system module having at least M sensor systems and at least one valve control mechanism, the at least one valve control mechanism arranged to control communication of the pressurizing gas; adding a liquid perifusate material to each of the N receptacles; mechanically coupling the perifusate reservoir module to the perifusion chamber module, the mechanical coupling forming a gasketed seal between the selected ones of the N receptacles with corresponding ones of the M microperifusion channels; and electromechanically coupling the control system module to the perifusion chamber, said electromechanical coupling causing each of the M sensor systems to be located in proximity to a respective one of the M microperifusion channels, said electromechanical coupling providing an electronic signal path to carry control signals to at least one valve.

Example A-2 may include the subject matter of Example A-1, and alternatively or additionally any other example herein, and further comprise: adding at least one sample of biological material to each of the M microperifusion channels; adding at least one dye to each of the M microperifusion channels; and executing at least one microperifusion test cycle, the at least one microperifusion test cycle spanning a selected time duration.

Example A-3 may include the subject matter of Example A-2, and alternatively or additionally any other example herein, and further comprise: directing a first valve to increase pressure in the perifusate reservoir module, the increased pressure causing at least some of the liquid perifusate material to flow in at least one of the M microperifusion channels; directing a first sequence of source signals to be emitted from at least one source sensor of the M sensor systems, the first sequence of source signals passing into the liquid perifusate material flowing in the at least one of the M microperifusion channels; directing a first response sensor that is paired a corresponding source sensor of the M sensor systems to measure a first sequence of response signals, each one of the first sequence of response signals responsive to at least one of the first sequence of source signals; and generate at least one value based on an accumulation of measured response signals, the at least one value representative of a determined property of the liquid perifusate material flowing in the at least one of the M microperifusion channels.

Example A-4 may include the subject matter of Example A-3, and alternatively or additionally any other example herein, wherein the at least one value indicates an oxygen consumption rate of the at least one sample of biological material.

Example A-5 may include the subject matter of Example A-3, and alternatively or additionally any other example herein, wherein a flow rate of liquid perifusate material flowing in the at least one of the M microperifusion channels is between about one-tenth microliter per minute and about 200 microliters per minute.

Example B-1 is a microperifusion system, comprising: at least one perifusate reservoir module, each of the at least one perifusate reservoir modules having N receptacles, and each of the at least one perifusate reservoir modules having at least one port arranged to communicate a pressurizing gas into or out from the respective perifusate reservoir module; for each of the at least one perifusate reservoir modules, a corresponding perifusion chamber module, each corresponding perifusion chamber module having M microperifusion channels, and each corresponding perifusion chamber module mechanically coupleable to one of the at least one perifusate reservoir modules to thereby form, when coupled, a sealed fluid communication between a selected first number of the N receptacles and a selected second number of the M microperifusion channels; and a control system module coupleable to each of the at least one perifusate reservoir modules and coupleable to each of the corresponding perifusion chamber modules, said control system module, when in operation, arranged to: control a flow of pressuring gas communicated into or out from the perifusate reservoir; and sense an effect of a microperifusion test operation occurring in each microperifusion channel.

Example B-2 may include the subject matter of Example B-1, and alternatively or additionally any other example herein, wherein the sensed effect is an oxygen consumption rate of at least one sample of biological material in at least one of the M microperifusion channels.

Example B-3 may include the subject matter of Examples B-1 to B-2, and alternatively or additionally any other example herein, and further comprise: pressure control logic to cause a perifusate material flowing in at least one of the M perifusion channels to the flow a selected rate of between about one-tenth microliter per minute and about 200 microliters per minute.

Example B-4 may include the subject matter of Examples B-1 to B-3, and alternatively or additionally any other example herein, wherein N is at least two times larger than M.

Example B-5 may include the subject matter of Examples B-1 to B-4, and alternatively or additionally any other example herein, and further comprise: a system of source sensors and response sensors, each response sensor pairable with a corresponding source sensor, and each response sensor arranged to capture light signal measurements responsive to light emitted by its corresponding source sensor; control logic arranged to direct each source sensor to emit light at a first selected time, the control logic further arranged to direct each response sensor to capture light signal measurements based on a second selected time; and math logic arranged to determine a rate of decay from the captured light signal measurements, the rate of decay indicative of the sensed effect.

Example C-1 is a control system for a microperifusion system, comprising: a sensor system, the sensor system including a plurality of source sensors and a plurality of response sensors, each source sensor pairable with a corresponding response sensor, each source sensor/response sensor pair arranged to communicate though a microperifusion channel; and at least one processor communicatively coupled to each source sensor/response sensor pair, the at least one processor arranged execute a test cycle having a determined duration, wherein during the test cycle, the at least one processor arranged to: direct a valve system to pressurize at least one receptacle of a perifusate reservoir, the perifusate reservoir having a plurality of N receptacles, the perifusate reservoir coupled to a microperifusion chamber in sealed fluid communication, the microperifusion chamber having a plurality of M microperifusion channels, said pressurized receptacle arranged to deliver a perifusate material to a respective one of the M microperifusion channels at a selected flow rate of less than about one-tenth microliter per minute to about 200 microliters per minute ($<\approx 0.1$ L/min to $\approx 200$ µL/min); direct a first sequence of source signals to be emitted from a first source sensor located in proximity to the respective one of the M microperifusion channels, the first sequence of source signals passing into a first perifusate material flowing at the selected flow rate in the respective one of the M microperifusion channels; direct a first response sensor that is paired with the first source sensor to measure a first sequence of response signals, each one of the first sequence of response signals responsive to at least one of the sequence of first source signals; and generate at least one value based on an accumulation of measured response signals, the at least one value representative of a determined property of the first perifusate material flowing at the selected flow rate in the respective one of the M microperifusion channels.

Example C-2 may include the subject matter of Example C-1, and alternatively or additionally any other example herein, wherein the test cycle is arranged for a continuous assessment of living biological material over a selected duration having a length as previously described herein.

Example C-3 may include the subject matter of Examples C-1 to C-2, and alternatively or additionally any other example herein, wherein the determined property is an oxygen consumption rate of at least one sample of biological material in at least one of the M microperifusion channels.

Example C-4 may include the subject matter of Examples C-1 to C-3, and alternatively or additionally any other example herein, wherein N is at least two times larger than M.

Example C-5 may include the subject matter of Example C-4, and alternatively or additionally any other example herein, wherein M is at least 96.

Example C-6 may include the subject matter of Example C-5, and alternatively or additionally any other example herein, wherein N receptacles are disposable receptacles.

Example C-7 may include the subject matter of Examples C-1 to C-6, and alternatively or additionally any other example herein, wherein the perifusate reservoir is disposable.

Example C-8 may include the subject matter of Examples C-1 to C-7, and alternatively or additionally any other example herein, wherein the at least one processor is further arranged to: direct the valve system to pressurize the perifusate reservoir to cause a first receptacle of the plurality of N receptacles, to deliver a test perifusate material into the at least one receptacle, wherein the at least one receptacle has a control perifusate material stored therein.

Example C-9 may include the subject matter of Example C-8, and alternatively or additionally any other example herein, wherein a first conduit between the first receptacle and the at least one receptacle has a first inside diameter, a second conduit between the at least one receptacle and an associated microperifusion channel has a second diameter, and the first diameter is larger than the second diameter.

Example C-10 may include the subject matter of Example C-9, and alternatively or additionally any other example herein, wherein the microperifusion chamber is formed, at least in part, from a three-dimensional printing process.

Example D-1 is a system for perifusing tissue samples, comprising: a plurality of perifusion chambers each configured for containing a different tissue sample; a first reservoir in fluid communication with each of the plurality of perifusion chambers, the first reservoir configured for containing a source perifusate; a source pressure port in fluid communication with the first reservoir, the source pressure port configured for enabling pressure within the first reservoir to be controlled, the pressure being controllable to drive movement, upon demand, of the source perifusate to each of the plurality of perifusion chambers at a controllable perifusion flow rate; a second reservoir in fluid communication with the first reservoir, the second reservoir configured for containing a test perifusate; and a transfer pressure port in fluid communication with the second reservoir, the transfer pressure port configured for enabling pressure within the second reservoir to be controlled, the pressure being controllable to drive movement, upon demand, of the test perifusate into the first reservoir, wherein the source perifusate comprises a control perifusate or a mixture of the control perifusate and the test perifusate.

Example D-2 may include the subject matter of Example D-1, and alternatively or additionally any other example herein, wherein the plurality of perifusion chambers comprises 96 perifusion chambers.

Example D-3 may include the subject matter of any of Examples D-1 and D-2, and alternatively or additionally any other example herein, wherein at least one of the plurality of perifusion chambers is transparent.

Example D-4 may include the subject matter of any of Examples D1 to D-3, and alternatively or additionally any other example herein, wherein the perifusion flow rate is no less than 0.25 µL/minute and no greater than 50 µL/minute.

Example D-5 may include the subject matter of any of Examples D-1 to D-3, and alternatively or additionally any other example herein, and further comprise: a tissue-effluent subsystem for collecting effluent perifusate from at least one of the plurality of perifusion chambers.

Example D-6 may include the subject matter of any of Examples D-1 to D-5, and alternatively or additionally any other example herein, and further comprise: for at least one of the plurality of perifusion chambers, a frit configured for holding the tissue sample disposed in the at least one of the plurality of perifusion chambers, while enabling the source perifusate to pass through the perifusion chamber.

Example D-7 may include the subject matter of any of Examples D-1 to D-6, and alternatively or additionally any other example herein, and further comprise: a measurement subsystem configured for measuring the oxygen consumption rate of at least one tissue sample disposed in at least one of the plurality of perifusion chambers.

Example D-8 may include the subject matter of Example D-7, and alternatively or additionally any other example herein, wherein the measurement subsystem comprises a device for measuring optical phosphorescent.

Example D-9 may include the subject matter of Example D-7, and alternatively or additionally any other example herein, wherein the measurement subsystem comprises an oxygen-sensitive fluorescent dye.

Example E-1 is a method for using any of Examples D-1 to D-9, and alternatively or additionally any other example herein.

Example F-1 is a non-transitory computer-readable medium having computer-executable instructions stored thereon that, if executed by one or more processors of a computing device, cause the computing device to perform one or more acts for using all or a portion of the system of any of Examples D-1 to D-9, and alternatively or additionally any other example herein.

Example G-1 is a microperifusion system, method, or device, wherein a perifusate reservoir module is provided, the perifusate reservoir module having N receptacles, and the perifusate reservoir module having at least one port arranged to communicate a pressurizing gas into or out from the perifusate reservoir module; a perifusion chamber module is provided, the perifusion chamber module having M microperifusion channels; a control system module is provided, the control system module having at least M sensor systems and at least one valve control mechanism, the at least one valve control mechanism arranged to control communication of the pressurizing gas; a liquid perifusate material is added to each of the N receptacles; mechanically coupling the perifusate reservoir module to the perifusion chamber module, the mechanical coupling forming a gasketed seal between the selected ones of the N receptacles with corresponding ones of the M microperifusion channels; and the control system module is electromechanically coupled to the perifusion chamber, said electromechanical coupling causing each of the M sensor systems to be located in proximity to a respective one of the M microperifusion channels, said electromechanical coupling providing an electronic signal path to carry control signals to at least one valve.

Example G-2 may include the subject matter of Example G-1, and alternatively or additionally any other example herein, and further comprise: a first coupling means to couple the perifusate reservoir module to the perifusion chamber module, and a second coupling means to couple the control system module to the perifusion module, wherein one or both of the first and second coupling means include at least one of screws, bolts, snap-fit connectors, friction-fit connectors, and hook-and-loop connectors.

Example G-3 may include the subject matter of any of Examples G-1 to G-2, and alternatively or additionally any other example herein, and further comprise: at least one first registration structure to guide a coupling of the perifusate reservoir module to the perifusion chamber module, and at least one second registration structure to guide a coupling of the control system module to the perifusion module, wherein one or both of the first and second registration features include a post, a protuberance, and an aperture.

Example G-4 may include the subject matter of any of Examples G-1 to G-3, and alternatively or additionally any other example herein, and further comprise: a pressure regulation means arranged to control pressure in the system, device, or method in a range of about 0.5 pounds per square inch (psi) to about two-and-one-half pounds per square inch ($\approx$0.5 psi to $\approx$2.5 psi).

Example G-5 may include the subject matter of any of Examples G-1 to G-4, and alternatively or additionally any other example herein, and further comprise: a pressure regulation means arranged to control perifusate flow at a rate in increments of about 0.2 microliters per minute (0.2 µL/min).

Example G-6 may include the subject matter of any of Examples G-1 to G-5, and alternatively or additionally any other example herein, and further comprise: at least one light-emitting diode (LED)/photoelectric diode (PED) pair structurally located about each microperifusion channel, wherein, at selected times, one of the at least one LEDs will emit light into its respective microperifusion channel, and at least one PED corresponding to the one of the at least one LEDs will measure received light.

Example G-7 may include the subject matter of any of Examples G-1 to G-6, and alternatively or additionally any other example herein, and further comprise: a photo-sensitive dye arranged in at least one microperifusion channel, the photo-sensitive dye arranged to generated light responsive to a reaction caused by the liquid perifusate material in the microperifusion channel flowing about a tissue or cell sample in the microperifusion channel.

Example G-8 may include the subject matter of any of Examples G-1 to G-7, and alternatively or additionally any other example herein, and further comprise: a cooling means to maintain the perifusate material at a selected temperature, the selected temperature being about 37 degrees Celsius or less.

Example G-9 may include the subject matter of any of Examples G-1 to G-8, and alternatively or additionally any other example herein, and further comprise: a plurality of perifusate receptacles formed in the perifusate chamber module, wherein each perifusate receptacle is sterilizable.

Example G-10 may include the subject matter of any of Examples G-1 to G-9, and alternatively or additionally any other example herein, and further comprise: a plurality of perifusate receptacles formed in the perifusate chamber module, wherein each perifusate receptacle is disposable.

Example G-11 may include the subject matter of any of Examples G-1 to G-10, and alternatively or additionally any other example herein, and further comprise: a plurality of perifusate receptacles formed in the perifusate chamber module, wherein each perifusate receptacle is a test tube having a volume of nine milliliters (9 mL).

Example G-12 may include the subject matter of any of Examples G-1 to G-11, and alternatively or additionally any other example herein, and further comprise: one or more gaskets arranged at an interface between the perifusate reservoir module and the microperifusion chamber module.

Example G-13 may include the subject matter of any of Examples G-1 to G-12, and alternatively or additionally any other example herein, and further comprise: at least one port arranged to receive the pressurizing gas.

Example G-14 may include the subject matter of any of Examples G-1 to G-13, and alternatively or additionally any other example herein, and further comprise: a single port arranged to receive the pressurizing gas.

Example G-15 may include the subject matter of any of Examples G-1 to G-14, and alternatively or additionally any other example herein, and further comprise: a plurality of conduits arranged in the perifusion chamber module to pass the liquid perifusate material, wherein passage of the liquid perifusate material is controllable by pressurizing one or more receptacles of the perifusate reservoir module.

Example G-16 may include the subject matter of any of Examples G-1 to G-15, and alternatively or additionally any other example herein, and further comprise: a plurality of conduits arranged in the perifusion chamber module to pass the liquid perifusate material, the plurality of conduits including a first conduit having a first internal diameter and a second conduit having a second internal diameter, the first internal diameter being smaller than the second internal diameter.

Example G-17 may include the subject matter of any of Examples G-1 to G-16, and alternatively or additionally any other example herein, wherein any one or more of the perifusate reservoir module, the perifusion chamber module, and a housing for the control system module is formed by a three-dimensional (3D) solid stereolithography process.

Example G-18 may include the subject matter of any of Examples G-1 to G-17, and alternatively or additionally any other example herein, wherein the perifusate reservoir is formed by a three-dimensional (3D) solid stereolithography process.

Example G-19 may include the subject matter of any of Examples G-1 to G-18, and alternatively or additionally any other example herein, wherein the system, method, or device has no peristaltic pump.

Example G-20 may include the subject matter of any of Examples G-1 to G-19, and alternatively or additionally any other example herein, wherein each microperifusion channel has transparent or translucent walls.

Example G-21 may include the subject matter of any of Examples G-1 to G-20, and alternatively or additionally any other example herein, wherein a tissue sample in each microperifusion channel includes ten or fewer islets.

Example G-22 may include the subject matter of any of Examples G-1 to G-21, and alternatively or additionally any other example herein, wherein a single test cycle is arranged to generate more than one thousand test profiles.

Example G-23 may include the subject matter of any of Examples G-1 to G-22, and alternatively or additionally any other example herein, wherein a native three-dimensional structure of tissue under test in each microperifusion channel is preserved.

Example G-24 may include the subject matter of any of Examples G-1 to G-23, and alternatively or additionally any other example herein, wherein at least one test cycle includes tissue of a specific person to develop a personalized medical test regimen for the specific person.

Example G-25 may include the subject matter of any of Examples G-1 to G-24, and alternatively or additionally any other example herein, wherein at least one test cycle is arranged to resolve glucose responses in oxygen consumption rate (OCR) by one (1) islet/channel.

Example G-26 may include the subject matter of any of Examples G-1 to G-25, and alternatively or additionally any other example herein, wherein at least one test cycle is arranged to generate dose-dependent responses of acetaminophen on oxygen consumption rate (OCR) by liver tissue.

Example G-26 may include the subject matter of any of Examples G-1 to G-25, and alternatively or additionally any other example herein, wherein the pressurizing gas is a pH-buffered physiological gas.

Example G-27 may include the subject matter of any of Examples G-1 to G-26, and alternatively or additionally any other example herein, wherein the pressurizing gas is a mixture of about five percent carbon dioxide and ambient air ($\approx 5\%$ $CO_2$, balance air).

Example G-28 may include the subject matter of any of Examples G-1 to G-27, and alternatively or additionally any other example herein, wherein the pressurizing gas, when applied, overlies separate perifusate receptacles of the perifusate reservoir module.

Example G-28 may include the subject matter of any of Examples G-1 to G-27, and alternatively or additionally any other example herein, wherein two adjacent microperifusion channels are arranged within about one half inch of each other.

Example G-29 may include the subject matter of any of Examples G-1 to G-28, and alternatively or additionally any other example herein, wherein at least one wall structure of each microperifusion channel is less than about three millimeters ($\approx 3$ mm) thick.

Example G-30 may include the subject matter of any of Examples G-1 to G-29, and alternatively or additionally any other example herein, wherein the microperifusion chamber is constructed from a plastic material, an acrylic material, a composite material, or a glass.

Example G-31 may include the subject matter of any of Examples G-1 to G-30, and alternatively or additionally any other example herein, wherein the system, device, or method is arranged to study a microgram quantity of cultured tissues such as liver slices and pancreatic islets or cultured cells immobilized on, or distributed within, a slurry of culture beads.

Example G-32 may include the subject matter of any of Examples G-1 to G-31, and alternatively or additionally any other example herein, wherein the microperifusion chamber module has eight microperifusion channels.

Example G-33 may include the subject matter of any of Examples G-1 to G-32, and alternatively or additionally any other example herein, wherein a gasket arranged at an interface between the perifusate reservoir module and the microperifusion chamber module permits two or more perifusate receptacles to share a common pressure.

Example G-34 may include the subject matter of any of Examples G-1 to G-33, and alternatively or additionally any other example herein, wherein a gasket arranged at an interface between the perifusate reservoir module and the microperifusion chamber module permits two or more perifusate receptacles to be pressurized to different pressures.

Example G-35 may include the subject matter of any of Examples G-1 to G-34, and alternatively or additionally any other example herein, wherein various receptacles of the perifusate reservoir module are separately pressurized, and wherein after the perifusate reservoir module is sealed, a first perifusate receptacle is pressurized to a first pressure, and a second perifusate receptacle is pressurized to a second pressure, the first pressure different from the second pressure, said differential pressure causing perifusate material to flow from one receptacle to another receptacle.

Example G-36 may include the subject matter of any of Examples G-1 to G-35, and alternatively or additionally any other example herein, wherein each microperifusion channel is arranged as a vertical tube having a frit, a tissue or cell sample, and an oxygen-sensitive dye located therein.

Example G-37 may include the subject matter of any of Examples G-1 to G-36, and alternatively or additionally any other example herein, wherein each microperifusion channel has an inside diameter of about 1.5 millimeters.

U.S. Provisional Patent Application No. 62/594,225, filed Dec. 4, 2017, is incorporated herein by reference, in its entirety.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microperifusion system, comprising:
a plurality of perifusate reservoir modules, each of the plurality of perifusate reservoir modules having a plurality of receptacles, and each of the plurality of perifusate reservoir modules having at least one port arranged to communicate a pressurizing gas into or out from the respective perifusate reservoir module;
for each of the plurality of perifusate reservoir modules, a corresponding perifusion chamber module, each corresponding perifusion chamber module having a plurality of microperifusion channels, and each corresponding perifusion chamber module mechanically coupleable to one of the plurality of perifusate reservoir modules to thereby form, when coupled, a sealed fluid communication between a selected first number of the plurality of receptacles and a selected second number of the plurality of microperifusion channels;
a plurality of gaskets, wherein each gasket of the plurality of gaskets is positioned at an interface between the respective perifusate reservoir module and the corresponding perifusion chamber module, wherein the plurality of gaskets is configured to seal an associated perifusate reservoir module of the plurality of perifusate reservoir modules,
wherein the plurality of receptacles of each of the plurality of perifusate reservoir modules includes a first perifusate receptacle and a second perifusate receptacle,
wherein the plurality of microperifusion channels of each of the perifusion chamber modules includes a first microperifusion channel;
a single pressure regulator that control flow rates between the first perifusate receptacle and a second perifusate receptacle, the first perifusate receptacle being pressurized to a first pressure, and the second perifusate receptacle being pressurized to a second pressure, wherein the first pressure is different from the second pressure, and said differential pressure causes perifusate material to flow from the first perifusate receptacle to the second perifusate receptacle;
a first conduit arranged between the first and second perifusate receptacles and configured to pass perifusate material between the first perifusate receptacle and the second perifusate receptacle, wherein the first conduit is a low-resistance transfer tube, wherein a portion of the first conduit is arranged within the perifusion chamber module;
a second conduit coupled to the first microperifusion channel and configured to pass perifusate material from the second perifusate receptacle to the first microperifusion channel, wherein the second conduit is a high-resistance source tube; and
wherein the single pressure regulator is configured to control a flow of pressuring gas communicated into or out from the perifusate reservoir module;
wherein the single pressure regulator is configured to control a flow rate of perifusate material from the first perifusate receptacle of the plurality of perifusate reservoir modules to the second perifusate receptacle of the plurality of perifusate reservoir modules; and
optical sensors coupled to the plurality of microperifusion channels including the first microperifusion channel and are configured to asses tissue during a microperifusion test operation occurring in each of the plurality of microperifusion channels including the first microperifusion channel.

2. The microperifusion system of claim 1, wherein the optical sensors are configured to sense an oxygen consumption rate of at least one sample of biological material in at least one of the plurality of microperifusion channels.

3. The microperifusion system of claim 1, wherein the control system further comprises: the single pressure regulator is configured pressure control logic to cause a perifusate material flowing in at least one of the plurality of microperifusion channels to flow at a selected rate of between about one-tenth microliter per minute and about 200 microliters per minute.

4. The microperifusion system of claim 1, further comprising:
- a system of source sensors and response sensors, each response sensor pairable with a corresponding source sensor, and each response sensor arranged to capture light signal measurements responsive to light emitted by its corresponding source sensor;
- wherein each source sensor is configured to emit light at a first selected time, wherein each response sensor is configured to capture light signal measurements based on a second selected time; and
- wherein a rate of decay is determined from the captured light signal measurements,
- wherein the system of source sensors and response sensors is coupled to at least one of the plurality of microperifusion channels including the first microperifusion channel.

\* \* \* \* \*